US006638236B2

(12) United States Patent
Thrash et al.

(10) Patent No.: US 6,638,236 B2
(45) Date of Patent: Oct. 28, 2003

(54) SELF-SEALED IRRIGATION SYSTEM

(75) Inventors: William J. Thrash, San Antonio, TX (US); Daniel L. Jones, San Antonio, TX (US)

(73) Assignee: Board of Regents of the University of Texas, Austin, TX (US)

(*) Notice: Subject to any disclaimer, the term of this patent is extended or adjusted under 35 U.S.C. 154(b) by 0 days.

(21) Appl. No.: 10/024,126

(22) Filed: Dec. 17, 2001

(65) Prior Publication Data

US 2002/0082544 A1 Jun. 27, 2002

Related U.S. Application Data

(60) Division of application No. 08/812,389, filed on Mar. 5, 1997, now Pat. No. 6,406,447, which is a continuation-in-part of application No. 08/379,219, filed on Jan. 27, 1995, now abandoned.

(51) Int. Cl.[7] .................................................. A61H 9/00
(52) U.S. Cl. ....................... 601/160; 601/166; 601/154; 604/290
(58) Field of Search ............................ 601/6, 154, 155, 601/159, 160, 162–166, 169; 604/174, 176, 289, 290, 292, 293, 313, 315, 305, 308

(56) References Cited

U.S. PATENT DOCUMENTS

| 2,113,253 A | 4/1938 | Gray |
| 2,272,481 A | 2/1942 | Rinkes et al. |
| 3,478,738 A | 11/1969 | Altman et al. |
| 3,489,141 A | 1/1970 | Warren, Jr. |
| 3,574,239 A | 4/1971 | Sollerud |
| 3,731,675 A | 5/1973 | Kelly |
| 3,732,580 A | 5/1973 | Fava |
| 4,353,359 A | 10/1982 | Milbauer |
| 4,940,056 A | 7/1990 | Heck et al. |
| 5,104,315 A | 4/1992 | McKinley |
| 5,145,367 A | 9/1992 | Kasten |
| 5,697,920 A | 12/1997 | Gibbons |
| 5,735,833 A | 4/1998 | Olson |
| 5,848,998 A | * 12/1998 | Marasco, Jr. ............... 604/290 |
| 5,941,859 A | 8/1999 | Lerman |

FOREIGN PATENT DOCUMENTS

| EP | 0505478 B1 | 12/1990 |
| WO | WO91/0879 | 6/1991 |

OTHER PUBLICATIONS

William J. Thrush, et al; *Self–Sealed Irrigation System*; copy of poster and other conference materials made available at a conference on or about Mar. 14, 1996 (9 pages).

* cited by examiner

Primary Examiner—Nicholas D. Lucchesi
Assistant Examiner—Quang D Thanh
(74) Attorney, Agent, or Firm—Myers Bigel Sibley & Sajovec

(57) ABSTRACT

A self-sealed irrigation system for supplying a treatment fluid to a treatment site is disclosed. The system includes a flexible containment member that has a delivery channel which delivers treatment fluid to the treatment site, a sealing channel supplied with a suction force, and a recovery channel. The delivery channel delivers the treatment fluid to the treatment site. The recovery channel removes spent treatment fluid from the treatment site. The sealing channel hermetically seals the containment member to the body surface surrounding the area to be treated. The containment member is designed such that any spent treatment solution which should by-pass the recovery channel is drawn into the sealing channel thereby preventing any treatment fluid from leaking to the outside environment. The containment member is connected to a suction pump which circulates treatment fluid through the treatment site and a reservoir which supplies the treatment fluid to the system.

12 Claims, 21 Drawing Sheets

FIG. 3
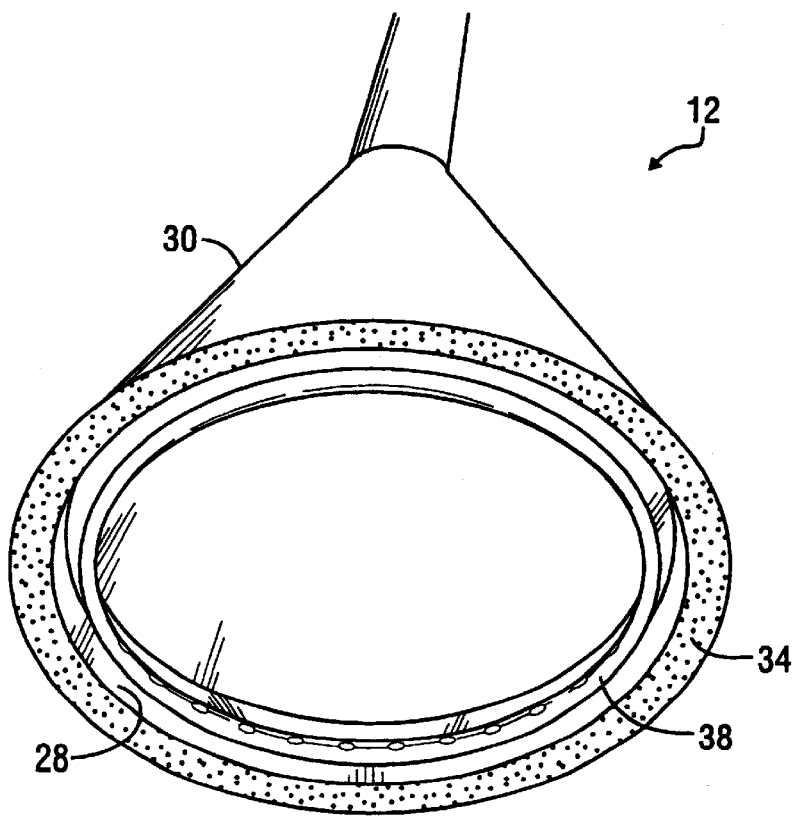
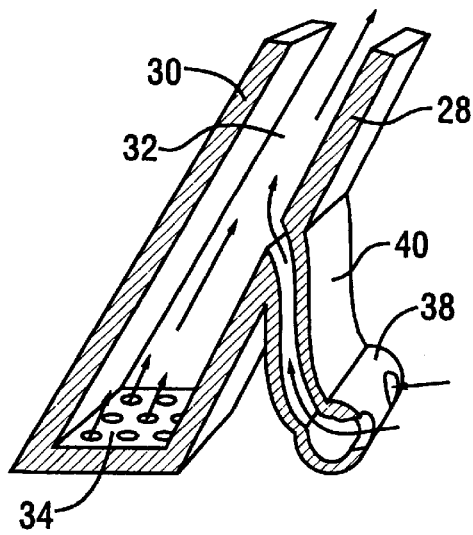
FIG. 4A
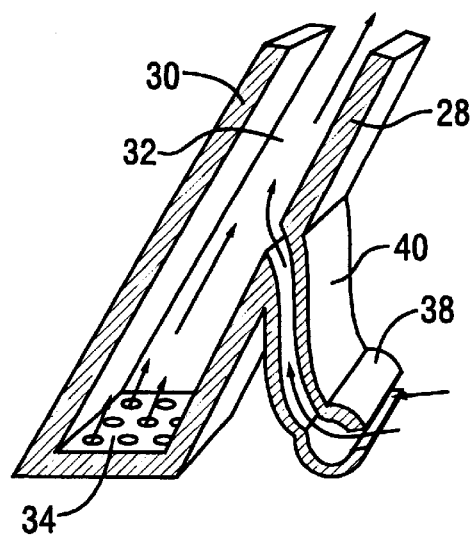
FIG. 4B

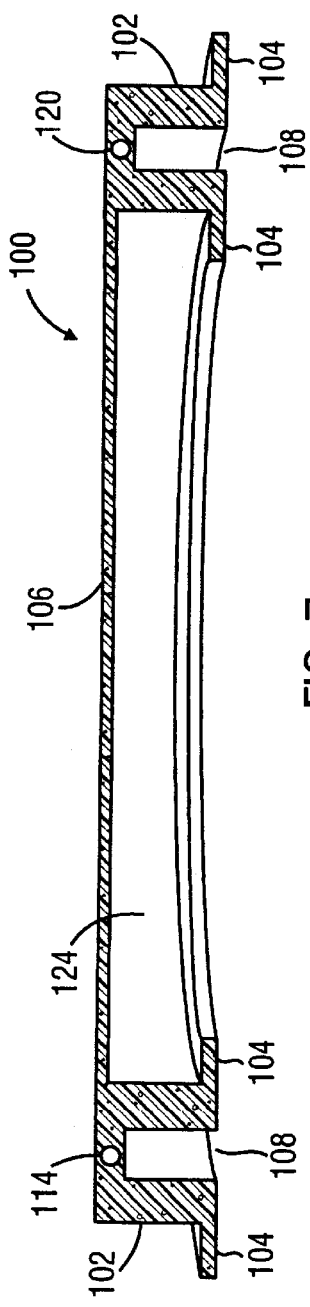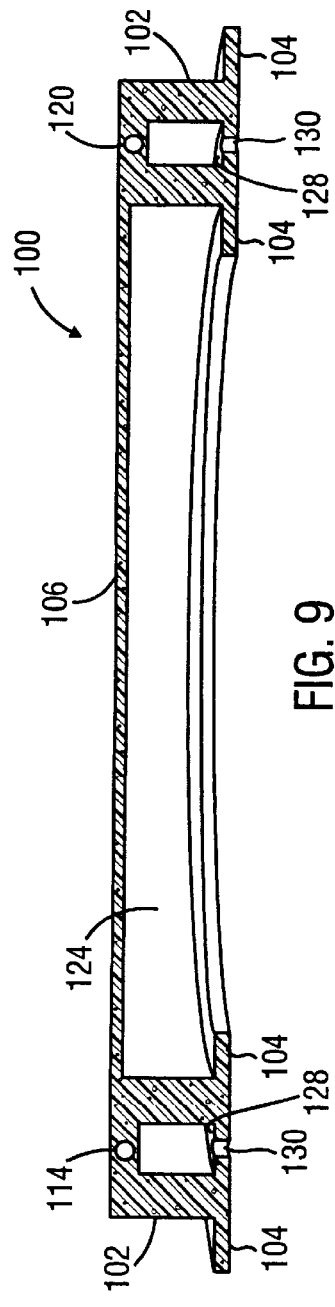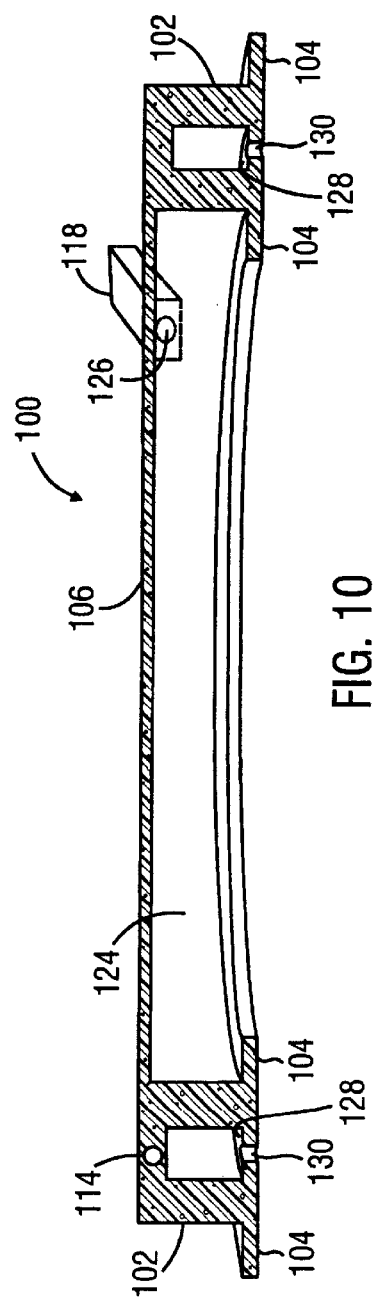

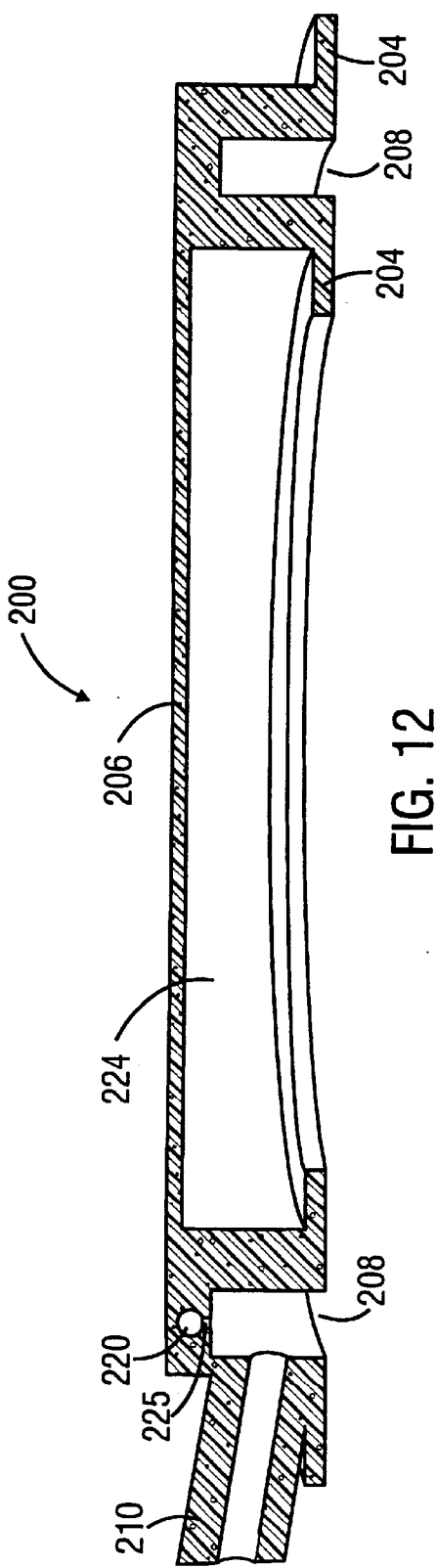
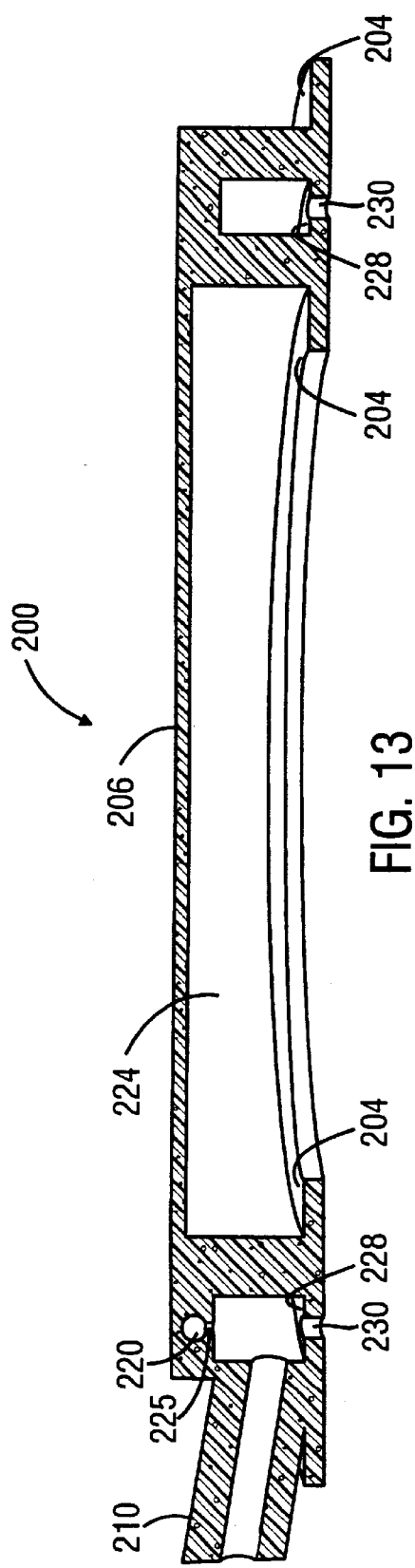

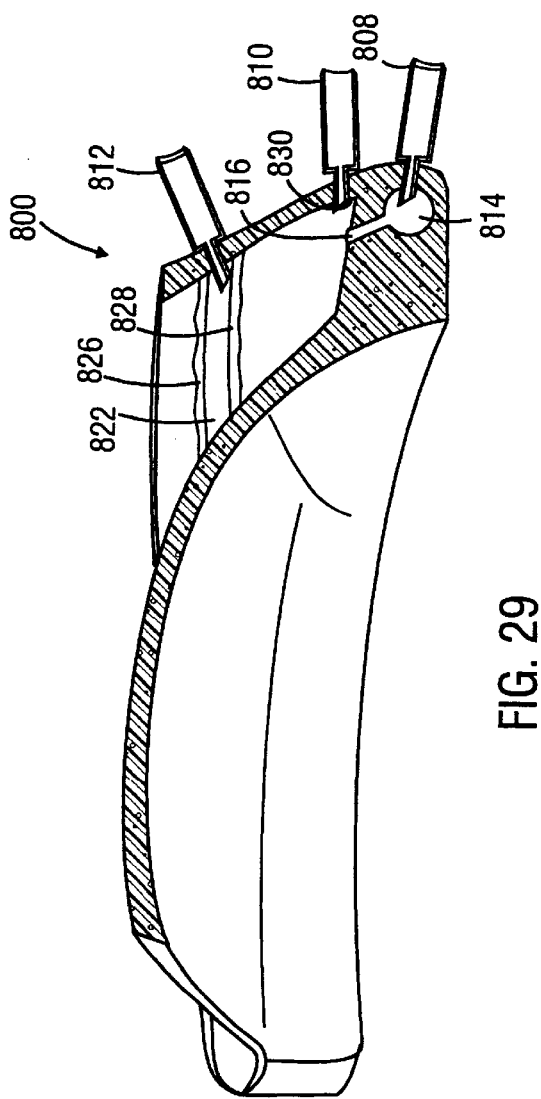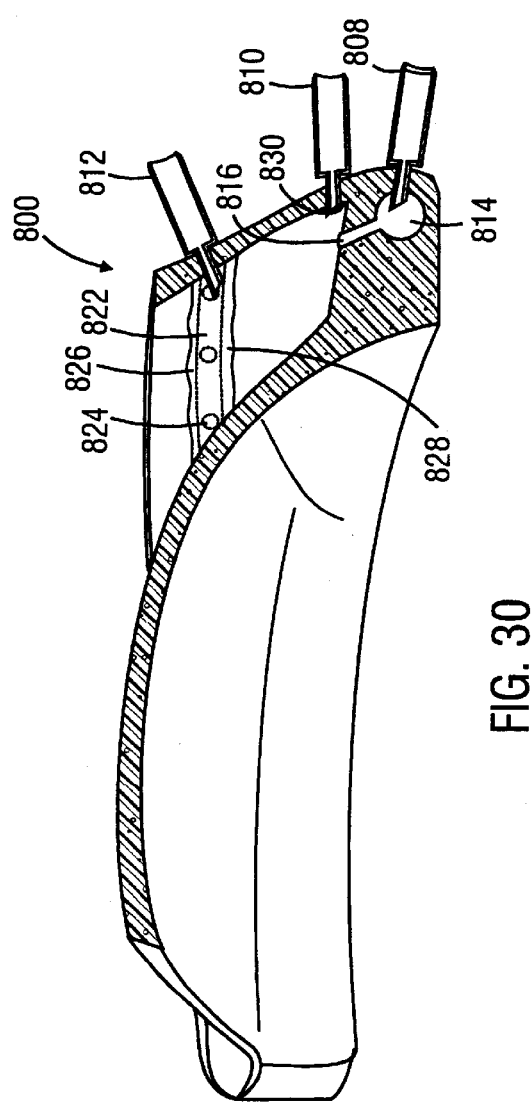

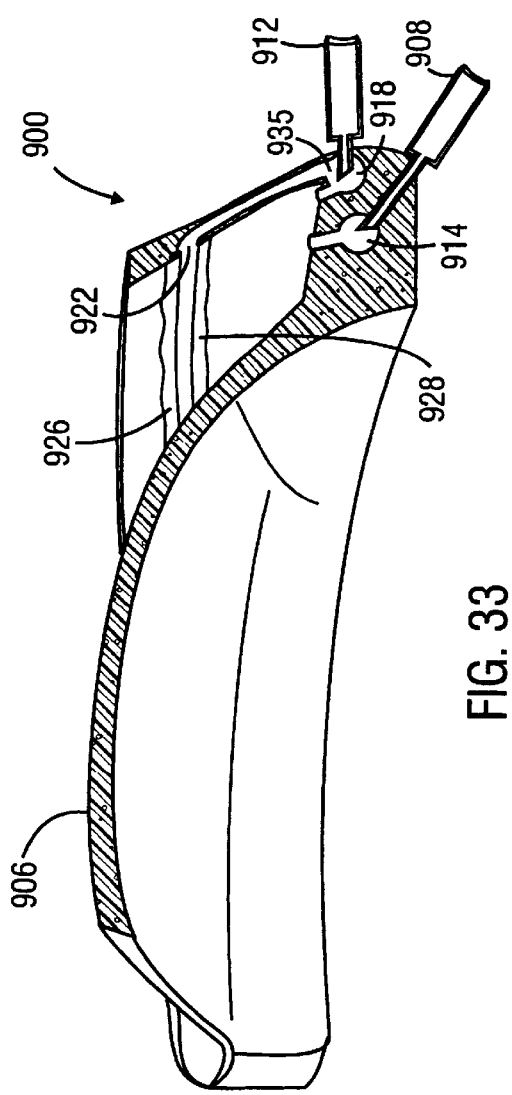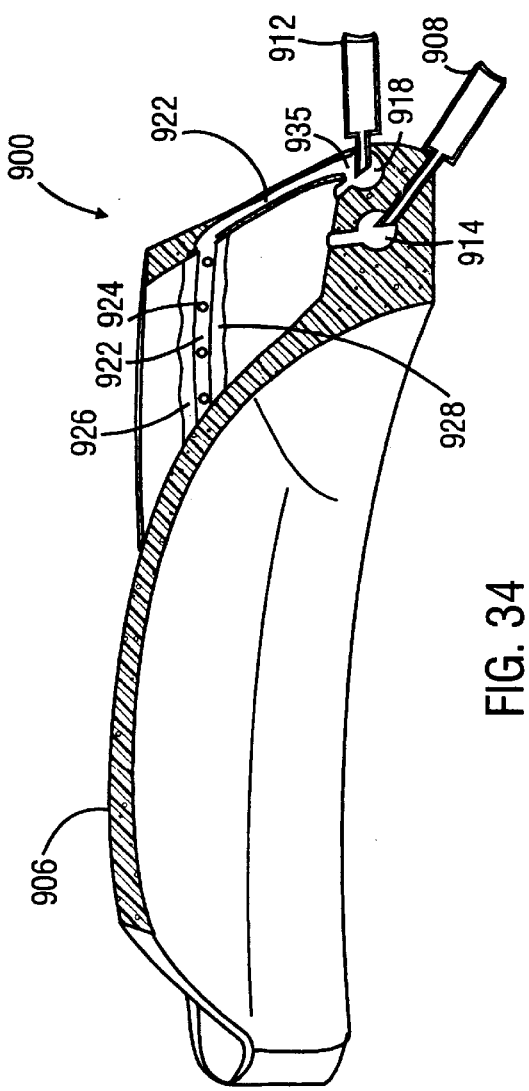

SELF-SEALED IRRIGATION SYSTEM

CROSS REFERENCE TO RELATED APPLICATIONS

The present application is a divisional of U.S. patent application Ser. No. 08/812,389, filed Mar. 5, 1997 and entitled SELF-SEALED IRRIGATION SYSTEM, now U.S. Pat. No. 6,406,447 which is a continuation-in-part of U.S. patent application Ser. No. 08/379,219, filed Jan. 27, 1995 now abandoned.

FIELD OF THE INVENTION

The present invention relates generally to irrigation systems, and more particularly, is directed to a self-sealed irrigation system adaptable for both intraoral and extraoral uses such as treating wounds, topical medication applications, site soakings, and the like.

BACKGROUND OF THE INVENTION

Known devices have been used for circulating treatment solutions in a closed system. For example, devices known as surgical wound dams have been used for the irrigation of surgical wounds. These devices are typically formed of rubber and are bound tightly to the wound site with a bandage. These devices include an oval-shaped rubber member adapted for delivering fluids to the surgical wound. The rubber delivery member has a permeable membrane on the surface opposite the surgical wound through which fluid is delivered to the wound and an outer annular wall which seals the oval-shaped rubber member to the skin. An inlet tube and an outlet tube connected to the rubber delivery member are provided for delivering fluid to, and removing fluid from, respectively, the surgical wound site so that fluid can be recirculated to that site.

A drawback of these devices is that they do not apply the treatment solution uniformly over the treatment site. A further drawback of these devices is that they are susceptible to leaks. They provide no means for removing treatment solution which may escape the suction force of the outlet tube and leak past the permeable membrane. Also, should leakage occur in such a device, it is likely to interfere with the seal formed between the annular wall and the treatment site.

Closed irrigation systems have also been used in the area of dental treatment. These systems were developed to provide effective and safe means of treating the dentoalveolar structures with chemotherapeutic rinses while avoiding ingestion of the rinses into the digestive tract of the patient.

The benefits of using oral chemotherapeutic rinses in the treatment of a variety of oral maladies has long been recognized. For example, fluoride solutions have been applied to teeth for years in order to prevent or arrest the progression of dental caries. More recently, chlorahexidine solutions have been developed to combat gingivitis and periodontal disease. These solutions, as well as many other oral rinses, are agents in the prevention, treatment, and healing process of dentoalveolar structures.

A drawback of prior oral irrigation systems is that they have a tendency to leak causing the chemotherapeutic rinses to be ingested into the digestive tract. This can cause undesirable side effects. For example, if ingested in a sufficient quantity and concentration, fluoride can cause gastrointestinal distress. Chlorahexidine can impair a person's ability to taste foods. The tremendous topical value of these agents is therefore mitigated by the potential side effects that might result if these agents are inadvertently ingested.

One known oral irrigation system utilizes a mouthpiece shaped to conform to the contours of the dentition. In this system, the treatment solution is pumped under high frequency pulsations to a chamber disposed within the mouthpiece. The chamber interconnects with a series of channels having outlets arranged along the mouthpiece so that the solution is ejected onto different areas of the teeth. The spent solution is evacuated through a second series of strategically placed outlets to a second chamber within the mouthpiece. An inlet tube and outlet tube connect the chambers of the mouthpiece to a pump which functions to circulate the solution through the mouthpiece in a closed system.

A drawback of this prior art device is that the space between the mouthpiece and the teeth is very small. This requires that an individualized mouthpiece be constructed for each patient. Thus, the device is incapable of being mass produced and hence is costly to manufacture. Furthermore, the mouthpiece of this device only covers the teeth and inter dental papillae thus limiting treatment to these areas. Accordingly, the device is not capable of covering, and thus not capable of treating, all of the entire dentoalveolar structures. Moreover, this prior art device suffers from the drawback of limiting both the volume and pressure of the solution which can be supplied to the treatment area.

Another drawback of this device is that it is not self-sealing. It relies on the suction emanating from the liquid return portion of the device, i.e., the second series of outlets, for both removing the spent solution and sealing the mouthpiece to the teeth and gums. This device does not provide a separate sealing mechanism which holds the mouthpiece in place and provides a barrier to the external environment. Consequently, the device is susceptible to leaks and is thus unreliable.

The present invention is directed to overcoming or at least minimizing some of the problems mentioned above.

SUMMARY OF THE INVENTION

In one embodiment of the present invention, a self-sealed irrigation system for general application is disclosed. The system supplies a treatment fluid, which may be either a liquid or a gas, to a treatment site utilizing a containment member which may take any one of the many forms described further herein. The flexible containment member includes a delivery channel which delivers the treatment fluid to the treatment site, a recovery channel supplied with a suction force, which removes the treatment solution from the treatment site and a sealing channel that hermetically seals the containment member to the treatment site. A delivery inlet coupling is provided which connects the delivery channel to a delivery pump external to the containment member. A recovery outlet coupling is also provided which connects the recovery channel to a suction pump external to the containment member. A suction outlet coupling is further provided for connecting the sealing channel to the suction pump. In one embodiment, the suction pump may also function as the delivery pump.

In another embodiment of the present invention, a self-sealed oral irrigation system for oral use is disclosed. It includes a reservoir of treatment fluid, a suction pump and a generally U-shaped mouthpiece which is formed to cover the dentoalveolar structure to be treated. The mouthpiece includes a delivery channel having a plurality of holes which deliver treatment fluid to the dentoalveolar structure to be treated, a recovery channel supplied with a suction force for removing the spent treatment solution, and a sealing channel which surrounds the dentoalveolar structure and hermetically seals the mouthpiece to the patient's gums. The recovery channel has a plurality of holes equally spaced along the perimeter of the mouthpiece through which spent treatment solution is removed from the dentoalveolar structure. The sealing channel may either be open or closed having a plurality of suction ports. A suction pump is connected to the mouthpiece via couplings and is coupled to a fluid reservoir.

The present invention also provides a method of irrigating a treatment site with a treatment fluid in a closed system. The method includes the steps of hermetically sealing the treatment site from an outside environment with a sealing means utilizing a suction force, delivering treatment fluid from a reservoir to the treatment site and applying the treatment fluid to the treatment site. The method also includes the steps of removing spent treatment solution from the treatment site through a recovery means. Any spent treatment solution which may have escaped the recovery means is then removed through the sealing means which preferably surrounds the entire treatment site, so as to prevent leakage of the spent treatment solution to the outside environment. The method also includes the step of purifying spent treatment solution for recirculation through the system.

BRIEF DESCRIPTION OF THE DRAWINGS

The foregoing and other features of the present invention will be best appreciated with reference to the detailed description of the invention, which follows when read in conjunction with the accompanying drawings, wherein:

FIG. 3 is a bottom perspective view of the containment hood shown in FIG. 2.

FIG. 4A is a partial enlarged view of one embodiment of the sealing means and treatment solution removal means portion of the containment hood shown in FIG. 2.

FIG. 4B is a partial enlarged view of another embodiment of the sealing means and treatment solution removal means portion of the containment hood shown in FIG. 2.

FIG. 7 is a cross-sectional view of the flexible containment member shown in FIG. 6 taken along line 7—7.

FIG. 9 is a cross-sectional view of yet another embodiment of the flexible containment member having a three channel design according to the present invention.

FIG. 10 is yet another cross-sectional view of another embodiment of the flexible containment member having a three channel design according to the present invention.

FIG. 12 is a cross-sectional view of the containment member shown in FIG. 11 taken along line 12—12.

FIGS. 13–15 are cross-sectional views of three other embodiments of the flexible containment member having a two channel design.

FIG. 29 is a partial cross-sectional partial perspective view of another embodiment of the mouthpiece having a three channel design according to the present invention.

FIG. 30 is a partial cross-sectional partial perspective view of yet another embodiment of the mouthpiece having a three channel design according to the present invention.

FIG. 33 is a partial cross-sectional partial perspective view of the embodiment of the mouthpiece shown in FIG. 31 taken along line 33—33.

FIG. 34 is a partial cross-sectional partial perspective view of another embodiment of the mouthpiece having a two channel design according to the present invention.

DETAILED DESCRIPTION OF THE INVENTION

The present invention is directed to a sealed irrigation system which can be used in a variety of applications. One embodiment of the invention has a general application. This embodiment will be described first. A second embodiment of the invention has a more specific application, namely for use in dental treatment. This latter embodiment will be described second.

Figure 1:
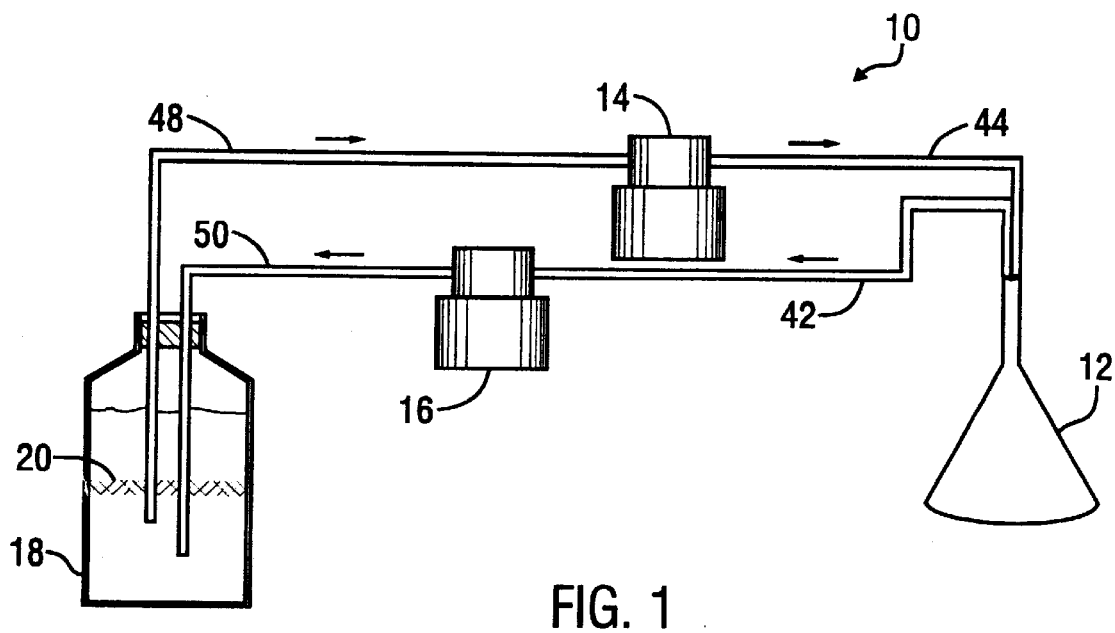
FIG. 1 is a diagram of a recirculating sealed irrigation system for general application according to the present invention.

Turning now to the drawings and referring initially to FIG. 1, one embodiment of a sealed irrigation system according to the present invention is shown generally by reference numeral 10. The system 10 includes a containment hood 12, a delivery pump 14, a suction pump 16, and a solution reservoir 18 having a filter 20. As those of ordinary skill in the art will appreciate, the functions of the delivery pump 14 and the suction pump 16 may be performed by a single vacuum pump.

Figure 2:
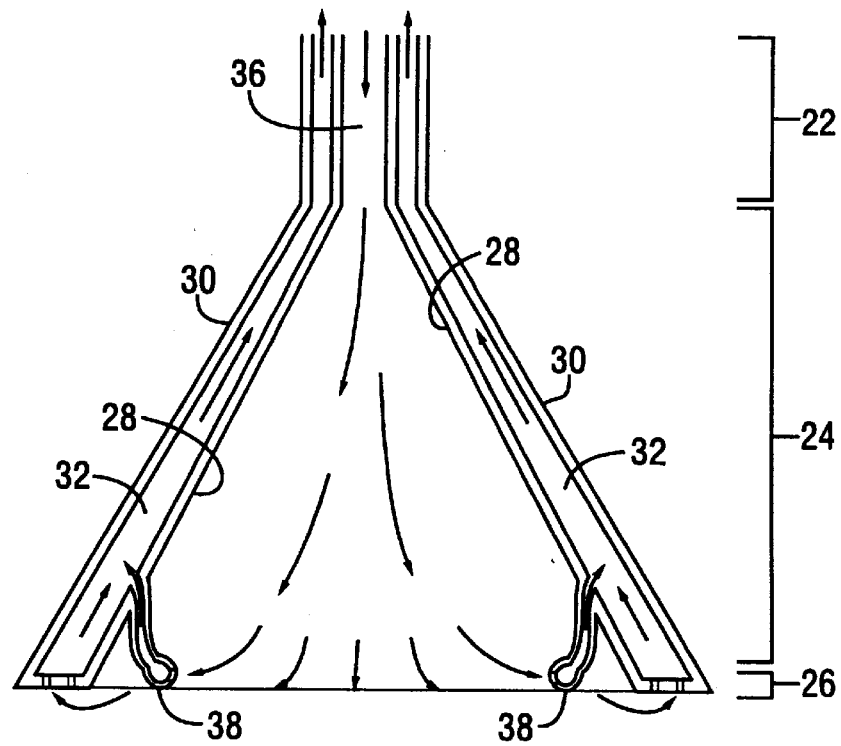
FIG. 2 is a cross-sectional view of a containment hood used in the recirculating sealed irrigation system shown in FIG. 1.

The containment hood 12 is shaped in the form of an inverted funnel having a neck portion 22, a conical portion 24, and an outer rim portion 26 and is designed to fit around the site to be treated, as shown in FIG. 2. The containment hood 12 is defined by an inner wall 28 and an outer wall 30, which are substantially parallel to one another at the neck portion 22, as shown in FIG. 2. In the conical portion 24, the inner wall 28 and outer wall 30 diverge slightly from one another. Intake channels 32 are formed between the inner wall 28 and the outer wall 30 which, as will be explained further below, are connected to the suction pump 16 so as to provide a vacuum stream which produces suction to hold the containment hood 12 in place and seal it to the treatment site of the patient. The intake channels 32 also function to uptake excess treatment solution, as will be explained further below. The containment hood 12 is preferably formed of a flexible material, such as Silastic® silicon rubber manufactured by Dow-Corning.

A flexible disk-shaped membrane 34 having a plurality of apertures is disposed at the outer rim portion 26 of the containment hood 12 between the inner wall 28 and the outer wall 30, as shown in FIG. 3. The flexible membrane 34 is preferably formed of rubber and may be integrally attached to the inner and outer walls 28 and 30 or alternatively may be removable. The flexible disk-shaped membrane 34 functions as a sealing ring which prevents leakage of the treatment solution to the outside environment.

A delivery channel 36 is provided at the neck portion 22 of the containment hood 12 which supplies a stream of treatment solution to the treatment site at a high velocity and pressure, e.g., 30 psi, as shown in FIG. 2. As the stream of treatment solution exits the delivery channel 36 into the conical portion 24 of the containment hood 12, it dissipates forming a substantially uniform spray which is applied to the treatment site.

The treatment solution is removed from the treatment site by a flexible recovery ring 38 having a plurality of holes equally spaced around its perimeter, as shown in FIG. 3. The recovery ring 38 is preferably tube-shaped and formed of rubber. It is disposed within, and along the perimeter of, the outer rim portion 26 of the containment hood 12. The plurality of holes in the recovery ring 38 are arranged along the inside of the ring, as shown in FIGS. 3 and 4A. In an alternate embodiment, the recovery ring 38 has a cut-out section along the inside of the ring in lieu of the plurality of equally spaced holes, as shown in FIG. 4B. The recovery ring 38 is attached to the inner wall 28 via a conduit 40, as shown in FIGS. 4A and 4B. The conduit 40 provides a fluid communication path between the recovery ring 38 and the intake channel 32.

As the uniform spray of treatment solution is applied to the treatment site it is removed through the holes in the recovery ring 38, as indicated by the arrows in FIG. 2. The spent treatment solution is removed from the treatment site by suction provided by the vacuum stream in the intake channel 32 which is supplied to the recovery ring 38 via the conduit 40. Because the holes in the recovery ring 38 are disposed along the inside of the ring and not the bottom of the ring, the recovery ring does not form a hermetic seal with the treatment site. This configuration enables spent treatment solution to be quickly and easily removed from the treatment site without the system "backing up", i.e., the treatment solution is removed from the treatment site at least as quickly as it is delivered to the treatment site. Accordingly, wounds are repeatedly "rinsed" and tissue breakdown products and infection generated tissue fluids rapidly removed, thus aiding in healing the wound.

However, because a hermetic seal is not formed with the treatment site, some of the spent treatment solution might seep past the recovery ring 38. Leakage of the spent solution to the outside environment is prevented, however, by the seal formed between the flexible disk-shaped membrane 34 and the area surrounding the treatment site. Any spent treatment solution which should by-pass the recovery ring 38 will be drawn into the intake channel 32 through the flexible disk-shaped membrane 34. This design provides a completely closed system which contains the treatment solution to the treatment site and prevents leakage of the solution to the outside environment.

Returning to a description of the system, the intake channel 32 is connected to the suction pump 16 via a conduit 42 which is preferably formed of a thermoplastic material, as shown in FIG. 1. The delivery channel 36 is connected to the delivery pump 14 via a conduit 44, also formed of a thermoplastic material. The delivery pump 14 and the suction pump 16 are connected to the treatment solution reservoir 18 via conduits 48 and 50, respectively. The filter 20 is provided within the reservoir 18 for purifying the treatment solution.

The treatment solution is circulated through the system as follows: The treatment solution is drawn from the reservoir 18 through the conduit 48 by the delivery pump 14 which transmits the solution through the conduit 44 to the delivery channel 36. As the treatment solution exits the delivery channel 36 into the conical portion 24 of the containment hood 12, it dissipates into a substantially uniform spray which is applied to the treatment site. The spent treatment solution is removed through the holes in the recovery ring 38. The spent solution is drawn through the conduit 40 to the intake channel 32. Any spent solution which seeps past the recovery ring 38 is drawn into the intake channel 32 through the flexible disk-shaped membrane 34. The spent solution is then transmitted through the conduit 42 to the suction pump 16. The suction pump 16 in turn delivers the spent treatment solution to the reservoir 18. Before the treatment solution is recirculated through the system it passes through, and is purified by, the filter 20.

As will be appreciated by those of ordinary skill in the art, there are alternate ways to construct the system according to the present invention. For example, as described above, the delivery pump 14 and the suction pump 16 may be combined into a single vacuum pump. Furthermore, the reservoir 18 and filter 20 may be incorporated into the pump thus forming a single recirculating unit which can be connected to the containment hood 12. In an alternative construction, two suction pumps may be provided, one which is connected via a conduit to the recovering ring 38 for removing the spent treatment solution, and the other which is connected to the intake channel 32 for sealing the containment hood 12 to the treatment site.

Figure 5:
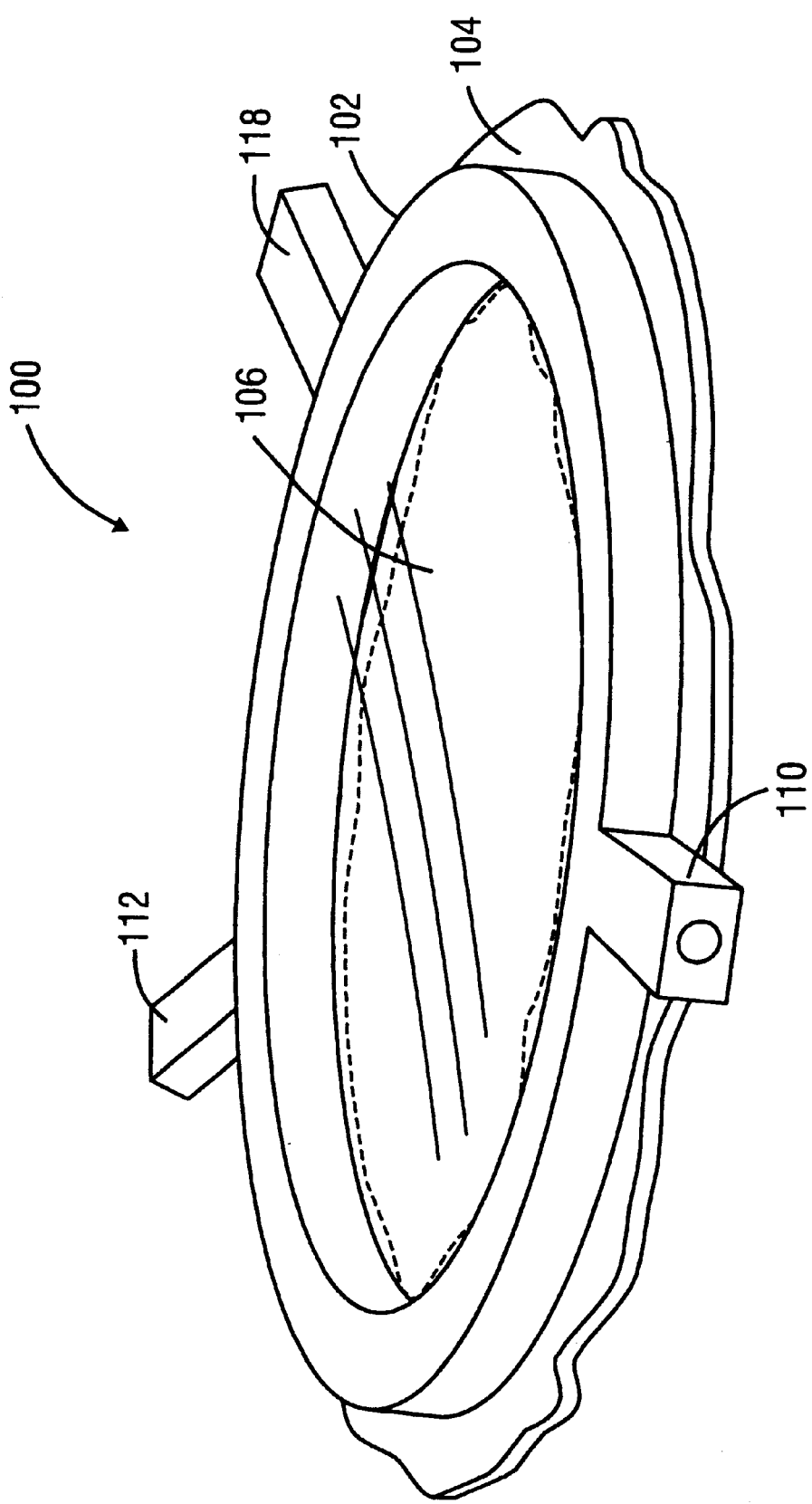
FIG. 5 is a perspective view of a flexible containment member having a three channel design according to the present invention.

A number of other embodiments of the general irrigation system according to the present invention will now be discussed. The first alternate embodiment is shown in FIG. 5. In this embodiment, a flexible containment member 100 is provided. The flexible containment member 100 is defined by a perimeter portion 102, which surrounds the area to be irrigated, a sealing surface 104, and a barrier member 106. The perimeter portion 102 preferably has a circular or oval shape, but may assume any desired shape.

Figure 6:
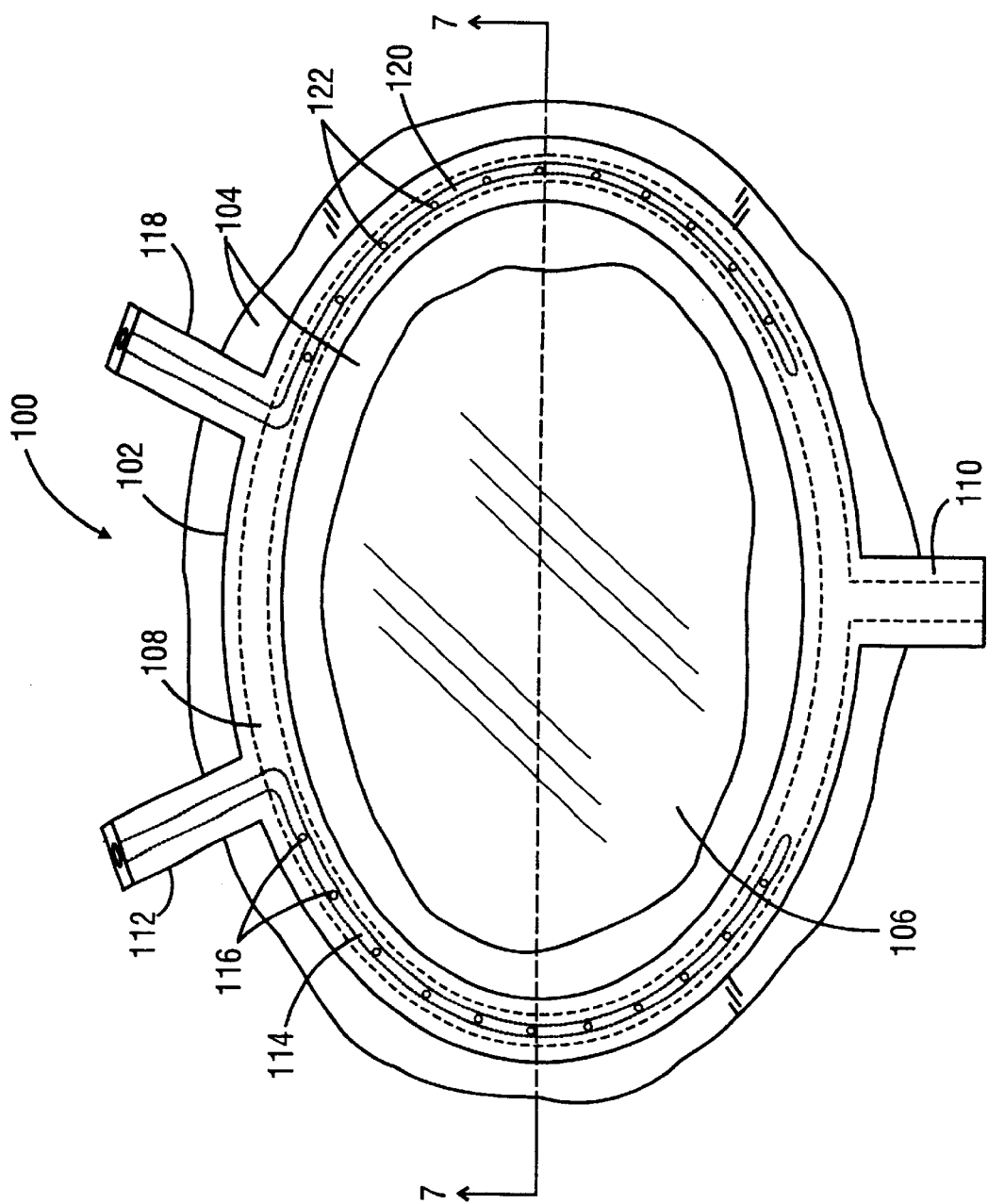
FIG. 6 is a top view of the flexible containment member shown in FIG. 5.

An open channel 108 (also referred to generally as the sealing channel 108) is formed along the periphery of the perimeter portion 102, as best seen in FIGS. 6 and 7. The open channel 108 delivers a suction force for securing the flexible containment member 100 to the body surface to be treated. The open channel 108 forms a hermetic seal between the flexible containment member 100 and also functions to recover any spent treatment solution not recovered by the recovery means discussed below.

A suction outlet coupling 110 (shown in FIGS. 5 and 6) is coupled to the perimeter portion 102 of the flexible containment member 100 and is in fluid communication with the open channel 108. The suction outlet coupling 110 is provided for coupling the flexible containment member 100 to a suction source, as further described below.

A delivery inlet coupling 112 is also coupled to the perimeter portion 102 of the containment member 100. The delivery inlet coupling 112 is in fluid communication with a delivery channel 114 formed in the perimeter portion 102, as shown in FIG. 6. The delivery channel 114 is located above the open channel 108 and extends along at least a portion of the periphery of the perimeter portion 102, as shown in FIGS. 6 and 7. A plurality of delivery ports 116 are formed in the delivery channel 114 that deliver treatment solution to the body surface to be treated, as shown in FIG. 6. The delivery inlet coupling 112 is provided for coupling the flexible containment member 100 to a fluid delivery source, as further described below.

A recovery outlet coupling 118 is further coupled to the perimeter portion 102 of the containment member 100, as shown in FIG. 6. The recovery outlet coupling 118 is in fluid communication with a recovery channel 120 formed in the perimeter portion 102. The recovery channel 120 is located above the open channel 108 and extends along at least a portion of the periphery of the perimeter portion 102, as shown in FIGS. 6 and 7. A plurality of recovery ports 122 are formed in the recovery channel 120 that recover the treatment solution delivered to the body surface treated, as shown in FIG. 6.

The suction outlet coupling 110, delivery inlet coupling 112, and recovery outlet coupling 118 are all preferably integrally formed parts of the flexible containment member 100, but as those skilled in the art will appreciate, these components may alternatively be attached to the flexible containment member 100 as separate members. If formed as separate members, these components are preferably formed of a thermoplastic material. Like the containment hood 12, the flexible containment member 100 is preferably formed of Silastic® silicon rubber.

The sealing surface 104 is a flat surface that form fits to the surface area to be treated when a suction force is applied to the open channel 108. It is defined by a pair of wing-shaped members that extend outward from the open channel 108. The sealing surface 104 extends around the entire periphery of the perimeter portion 102, as best seen in FIG. 6. The barrier member 106 is a thin fluid impermeable layer that contains the area enclosed by the perimeter portion 102.

The barrier member 106 contains the fluid within an area defined as the internal chamber 124, which is best seen in FIG. 7.

Figure 8:
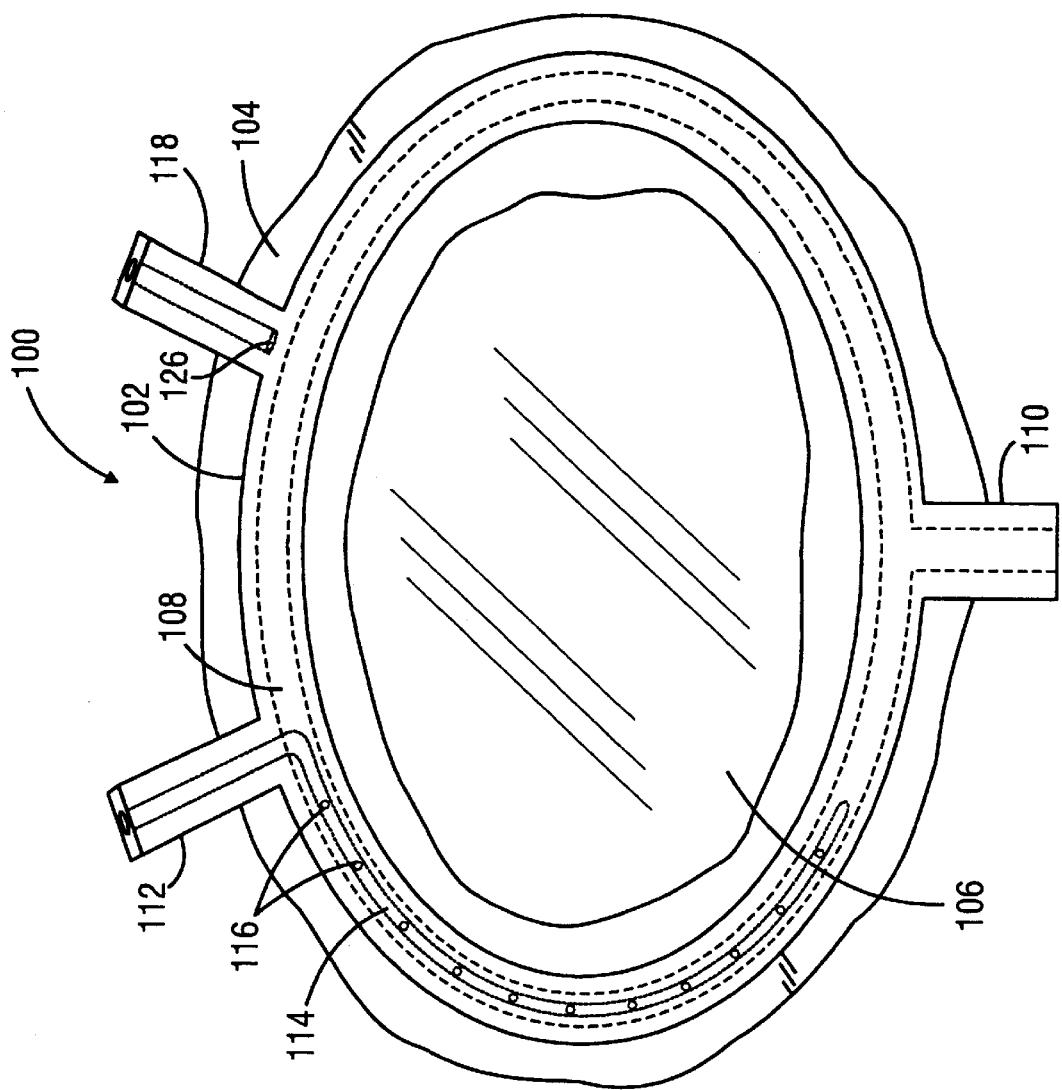
FIG. 8 is a top view of an alternate embodiment of the flexible containment member having a three channel design according to the present invention.

In another alternate embodiment of the present invention, the flexible containment member 100 has no recovery channel or corresponding recovery ports, as shown in FIG. 8. Rather, the recovery outlet coupling 118 has a port 126 which allows spent treatment solution to be removed from the treatment area.

In another embodiment of the present invention, the open channel 108 is replaced with a closed channel 128 having a plurality of ports 130, as shown in FIG. 9. In this configuration, the plurality of ports 130 supply the suction force that seals the flexible containment member 100 to the body surface. This configuration has application for patients that have sensitive or irritated skin around the area to be treated. The design minimizes the area of skin exposed to the suction force, while ensuring a sufficient seal.

The embodiment shown in FIG. 9 utilizes the design employing a recovery channel 120 and plurality of recovery ports 122. A modification of this design would be to replace the recovery channel 120 and plurality of recovery ports 122 with the single recovery port 126 shown in FIG. 8. This yet other embodiment of the present invention is shown in FIG. 10.

The embodiments shown in FIGS. 5–10 incorporate a three channel design, i.e., the delivery channel 114, recovery channel 120, and sealing channel 108 are separated inside the flexible containment member 100. These embodiments may alternatively incorporate a two channel design. In the two channel design, the recovery channel 120 and sealing channel 108 are connected to one another inside the flexible containment member 100. This modified design, as it applies to the various embodiments shown in FIGS. 5–10, is shown in FIGS. 11–15.

In the two channel design, there are only two couplings, a suction outlet coupling 210 and a delivery inlet coupling 212. The recovery outlet coupling 118 of the three channel design illustrated in FIGS. 5–10 is incorporated into the suction outlet coupling 210. The suction outlet coupling 210 supplies a suction force to both recovery channel 220 and sealing channel 208, as shown in FIG. 12. The recovery channel 220 is connected to the sealing channel 208 via conduit 225.

Figure 11:
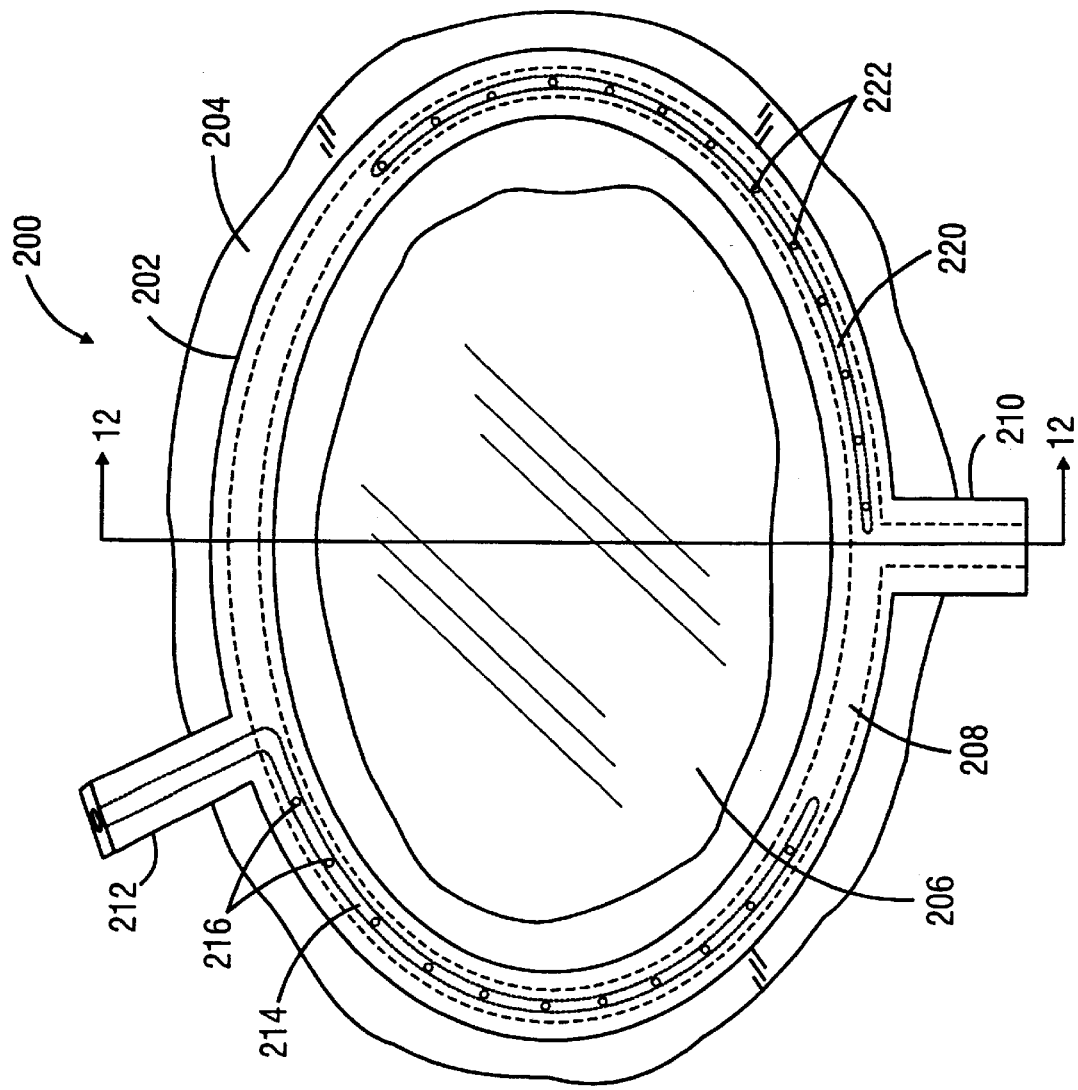
FIG. 11 is a top view of a flexible containment member having a two channel design.
Figure 14:
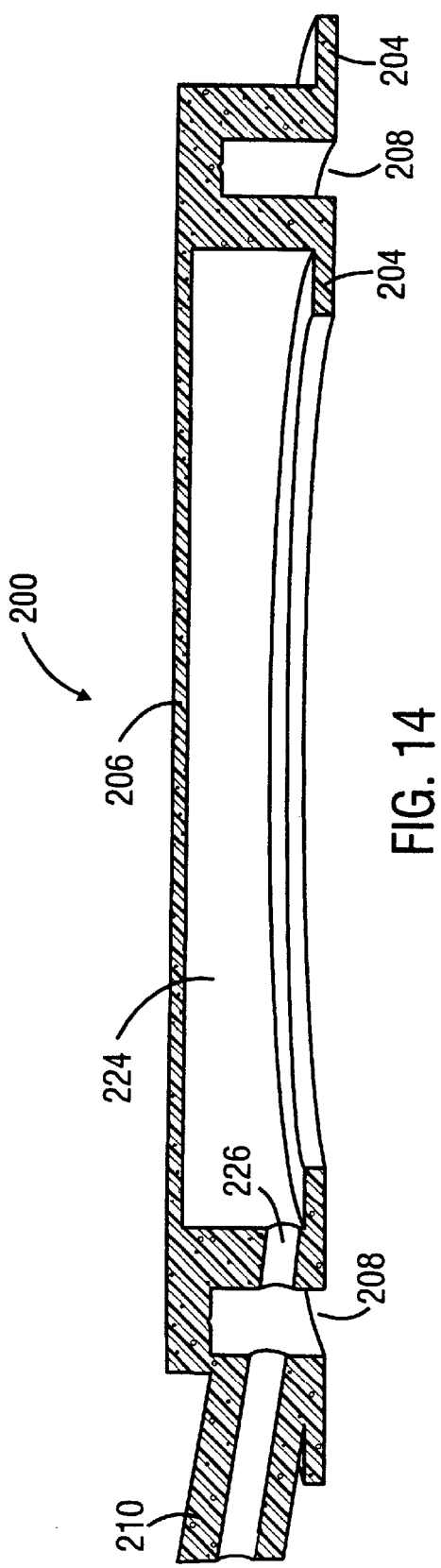
Figure 15:
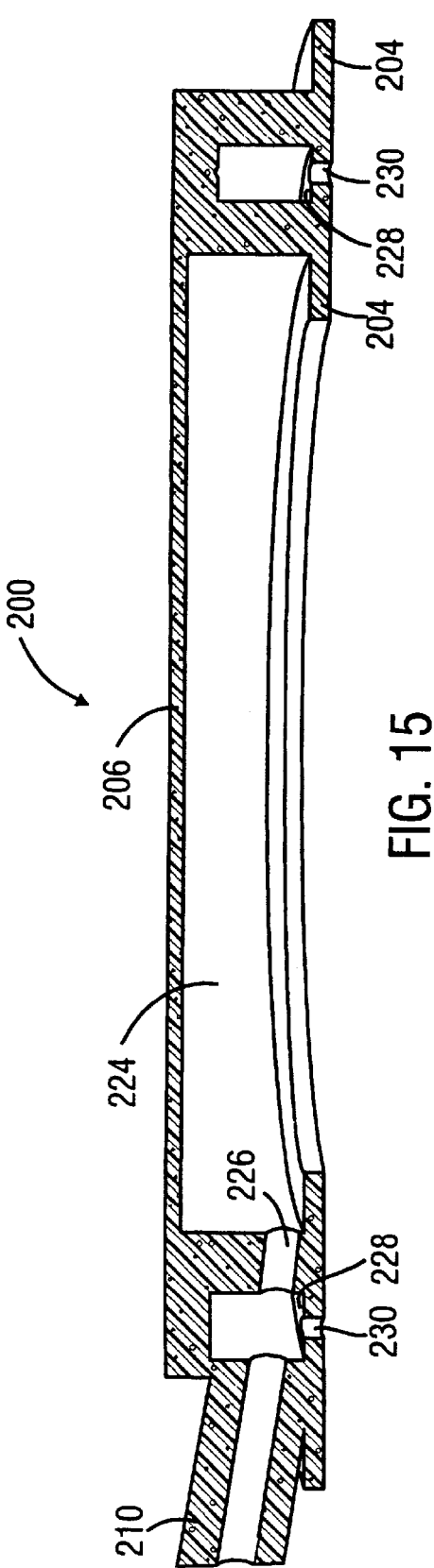

In the embodiment shown in FIGS. 11 and 12, the recovery channel 220 has a plurality of ports 222, and the sealing channel 208 is an open channel. In the embodiment shown in FIG. 13, the recovery channel 220 has a plurality of ports 222 (not shown), and the sealing channel 208 is a closed channel 228 having a plurality of ports 230. In the embodiment shown in FIG. 14, the recovery channel 220 and plurality of ports 222 are replaced with a single recovery port 226, and the sealing channel 208 is an open channel. In the embodiment shown in FIG. 15, the recovery channel 220 and plurality of ports 222 are replaced with a single recovery port 226, and the sealing channel 208 is a closed channel 228 having a plurality of ports 230.

Figure 16:
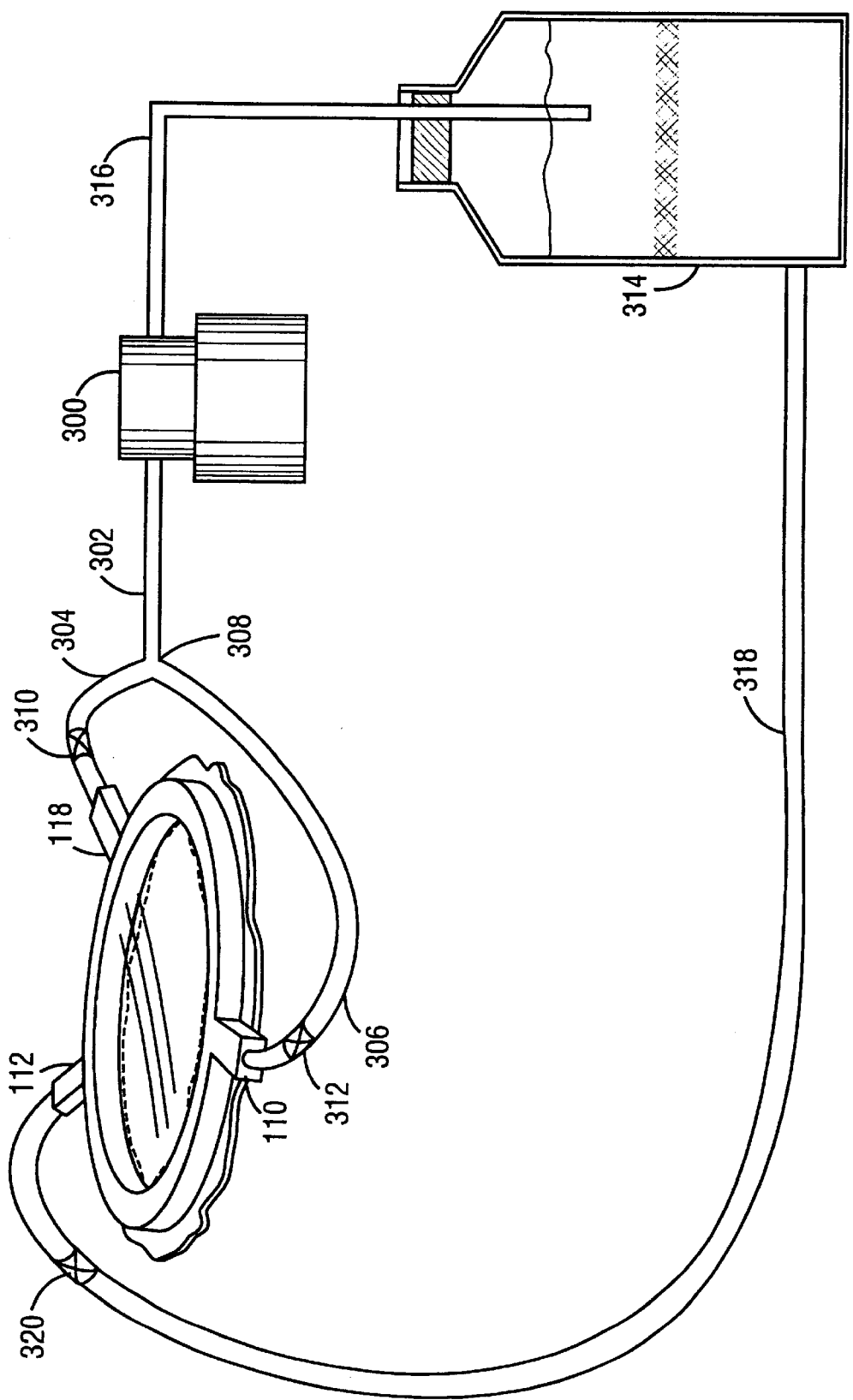
FIG. 16 is a diagram of an irrigation system employing the three channel design flexible containment member having a three channel design according to the present invention.

FIG. 16 illustrates the three channel configuration of the flexible containment member 100 connected to a vacuum pump 300. The vacuum pump 300 supplies a suction force to the recovery channel 120 and the sealing channel 108. The suction force is supplied to the recovery channel 120 via conduits 302 and 304 and supplied to the sealing channel 108 via conduits 302 and 306. The conduits 304 and 306 are connected at one end to the conduit 302 at juncture 308 and connected at the other end to the recovery outlet coupling 118 and the suction outlet coupling 110, respectively. Valves 310 and 312 disposed in conduits 304 and 306, respectively, are provided to regulate the supply of suction force to the recovery channel 120 and sealing channel 108, respectively. The valves 310 and 312 are preferably variable flow valves.

The vacuum pump 300 also supplies compressed air to a solution reservoir 314 via a conduit 316. The treatment solution is supplied under pressure from the solution reservoir 314 to the delivery channel via conduit 318, which is connected to the flexible containment member 100 at the delivery inlet coupling 112. A valve 320 disposed within the conduit 318 regulates the supply of the treatment solution to the treatment area. As those of ordinary skill in the art will appreciate, the functions of the vacuum pump 300 may be shared between a delivery pump and a separate suction pump, as shown in FIG. 1.

The treatment solution can either be passed through the treatment area or it may be confined to the treatment area under pressure. The treatment solution is preferably passed through the treatment area in cleansing operations. When it is desired to cause the treatment solution to be absorbed transdermally, however, then it is preferable to confine the treatment area under pressure.

The treatment solution is passed through the treatment area first by delivering the solution to the treatment area, and then by removing the treatment solution from the treatment area. This is accomplished by operating the vacuum pump 300 while the valves 310 and 320 are open. The valve 320 allows the treatment solution to be delivered to the treatment area, and the valve 310, by supplying a suction force to the treatment area, causes the treatment solution to be removed. During this operation, the valve 312 is open thereby supplying a suction force to the sealing channel 108 and sealing the flexible containment member 100 to the body surface.

The treatment solution is confined to the treatment area under pressure by opening the valves 312 and 320 and closing the valve 310. As discussed above, the valve 320 allows the treatment solution to be delivered to the treatment area, and the valve 312 supplies suction force to seal the flexible containment member 100 to the body surface. By closing the valve 310, the treatment solution cannot be removed from the internal chamber 124 (shown in FIGS. 7, 9 and 10) and thereby remains within the internal chamber 124 under pressure. When it is desired to remove the treatment solution from the internal chamber 124, the valve 310 is opened. As those of ordinary skill in the art will appreciate, a variety of different treatment methods are possible with the three channel design illustrated in FIG. 16. This is made possible by the adjustability of the valves 310, 312 and 320.

Figure 17:
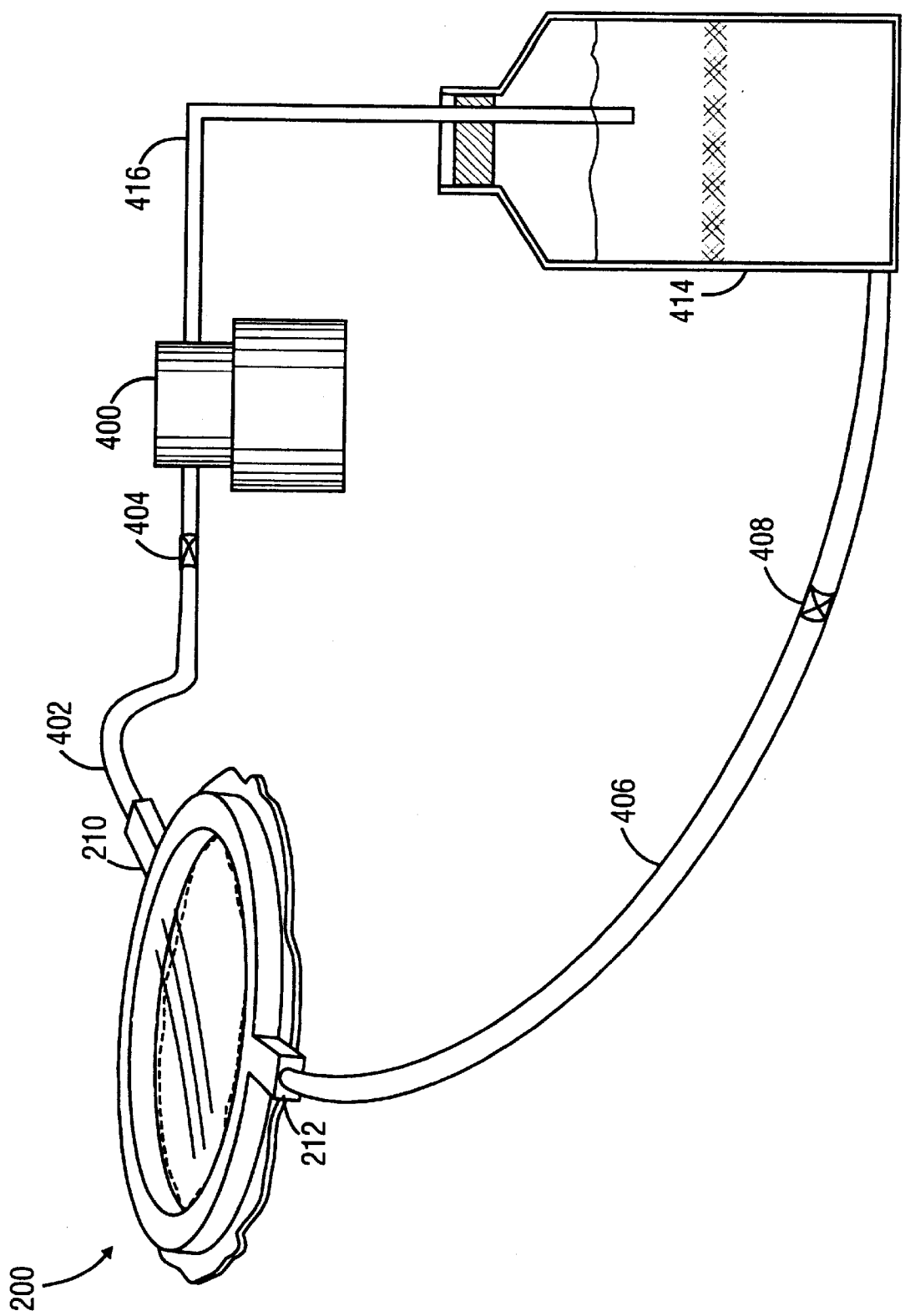
FIG. 17 is an irrigation system employing the flexible containment member having a two channel design according to the present invention.

FIG. 17 illustrates the two channel configuration of the flexible containment member 100 connected to the vacuum pump 400. In this configuration, the suction force is supplied from the vacuum pump 400 to the flexible containment member 200 via a single conduit 402. The conduit 402 delivers the suction force to the suction outlet coupling 210, which, as described above, in turn delivers the suction force to the recovery channel 220 and sealing channel 208. A valve 404, disposed in the conduit 402, is provided for turning the suction force on and off. The vacuum pump 400 supplies compressed air to solution reservoir 414 via conduit 416. The treatment solution is then delivered to the treatment area under pressure from the solution reservoir 414 via conduit 406. A valve 408, disposed in the conduit 406, is provided for regulating the supply of the treatment solution to the treatment area. With this configuration, the treatment solution may only be passed through the flexible containment member 200. Because the recovery channel 220 may not be shut off without also shutting off the supply of suction to the sealing channel 208, the treatment solution may not be confined to the internal chamber 224 under pressure with this arrangement.

The systems described above have universal application for the treatment of wounds, debridement, site soakings, topical administration of various liquid dedications as well as a variety of other applications. Other such applications include: rinsing for eye infections, rinsing for ear infections and wax removal, palliative irrigation for painful relief of gums, veterinary applications, hyperbaric oxygen delivery, delivery of antimicrobial rinses to many types of patients, treatment of athletes foot, treatment of infections in immune-compromised patients (e.g., HIV, organ transplants), localized treatment of bed sores, hand and feet sores of diabetic patients, etc.

Figure 18:
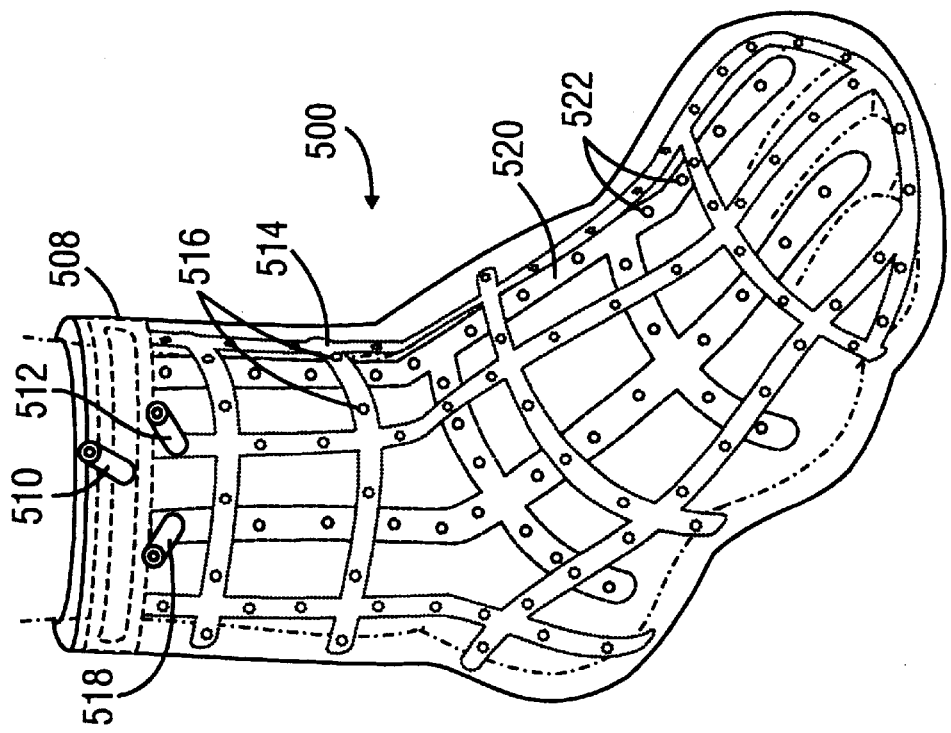
FIG. 18 shows a modification of the flexible containment member according to the present invention which is adapted to fit around the foot and ankle portion of a patient's leg.

The configuration of the flexible containment member 100 may be modified to enclose virtually any treatment site. One specialized configuration is shown in FIG. 18. In this embodiment, the containment member 100 takes the form of a boot 500 which fits over the foot and ankle of a patient. The boot 500 is provided with a delivery channel 514 having a plurality of ports 516, a recovery channel 520 having a plurality of ports 522, and a sealing channel 508, as well as all the other features of the above-described invention including a suction outlet coupling 510, a delivery inlet coupling 512, and a recovery outlet coupling 518. Furthermore, as those of ordinary skill in the art will appreciate, the boot 500 may take the form of any one or more of the embodiments described herein.

Figure 19:
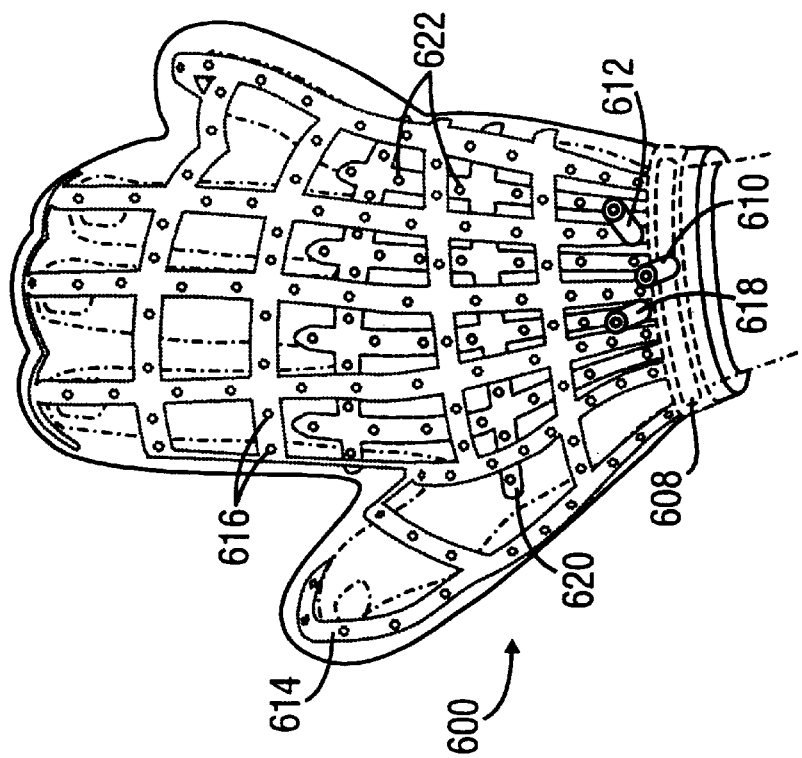
FIG. 19 shows a modified embodiment of the flexible containment member according to the present invention which is adapted to fit around the hand and wrist portion of a patient's hand.

Another specialized configuration is shown in FIG. 19. In this embodiment, the containment member 100 takes the form of a glove 600 which fits over the hand and wrist of a patient. The glove 600 is provided with a delivery channel 614 having a plurality of ports 616, a recovery channel 620 having a plurality of ports 622, and a sealing channel 608, as well as all the other features of the above-described invention including a suction outlet coupling 610, a delivery inlet coupling 612, and a recovery outlet coupling 618. Furthermore, as those of ordinary skill in the art will appreciate, the glove 600 may take the form of any one or more of the embodiments described herein.

Figure 20:
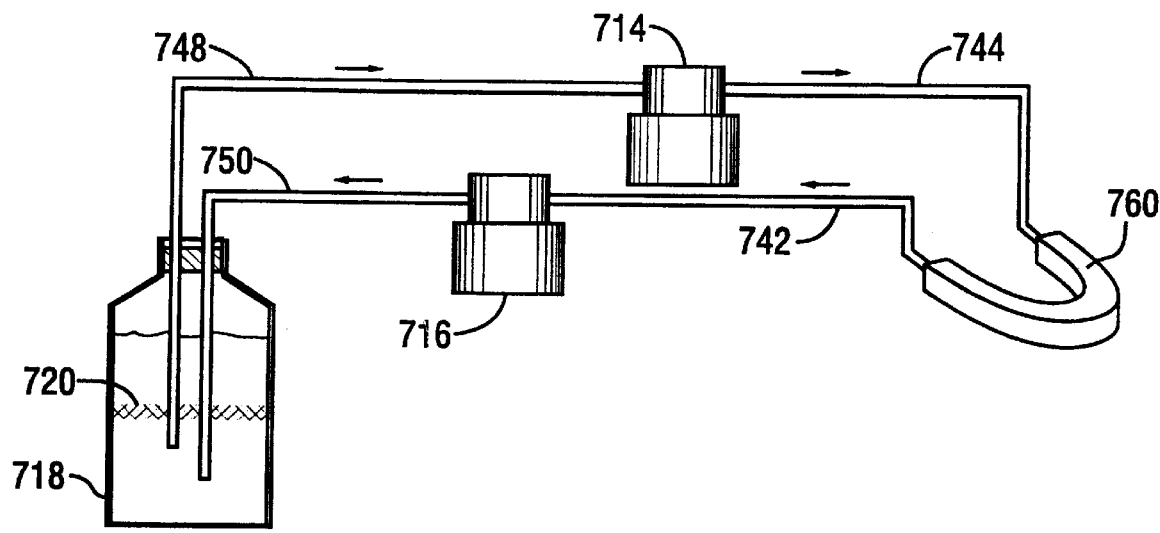
FIG. 20 is a diagram of a recirculating sealed oral irrigation system used for dental treatment according to the present invention.
Figure 21:
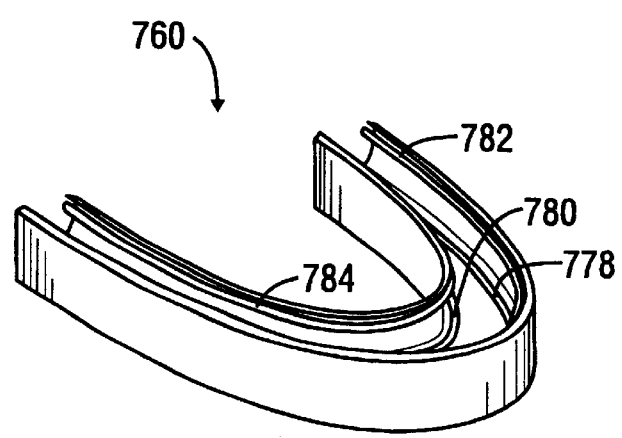
FIG. 21 is a top perspective partial cross-sectional view of a mouthpiece used in the recirculating sealed oral irrigation system shown in FIG. 20.

In yet another embodiment of the present invention, a recirculating sealed oral irrigation system according to the present invention is shown in FIG. 20. In this embodiment, the flexible containment member 100 is modified into a mouthpiece adaptable for covering dentoalveolar structures to be treated. Such a mouthpiece is shown generally in FIG. 20 by reference numeral 760. The mouthpiece 760 has a generally U-shaped configuration which corresponds to the shape of the appropriate dentoalveolar structures and is preferably formed of a thermoplastic material, such as medical grade silicone, as shown in FIG. 21. In the case of the upper jaw or maxilla, the mouthpiece 760 may be configured to cover the hard palate or only the teeth and gums depending on the treatment to be offered.

Figure 22:
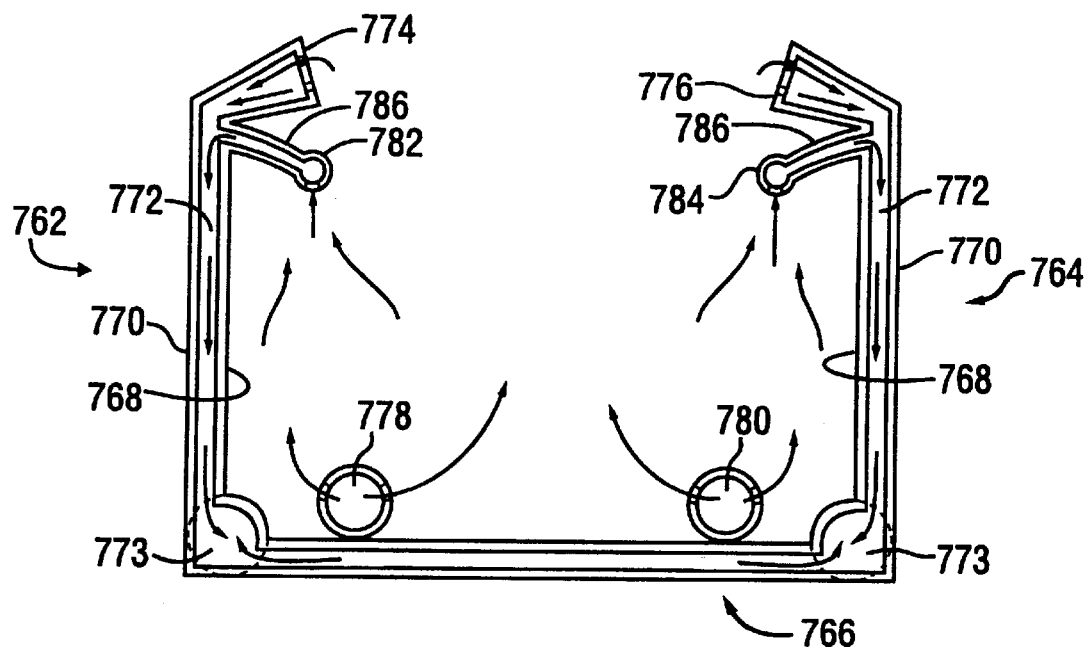
FIG. 22 is a cross-sectional view of the mouthpiece shown in FIG. 21.

The cross-section of the mouthpiece 760 is generally canal-shaped being defined by a pair of side walls 762 and 764 and a bottom wall 766 disposed between the side walls, as shown in FIG. 22. The pair of side walls 762 and 764 and the bottom wall 766 are in turn defined by an inner wall 768 and an outer wall 770. The inner wall 768 and the outer wall 770 are substantially parallel to one another. The space between the inner wall 768 and the outer wall 770 forms an intake channel 772 which is connected to the suction pump 716 via conduits 773 which are disposed along the perimeter of the mouthpiece 760.

The upper ends of each of the pair of side walls 762 and 764 project inwardly at a substantially right angle, so as to be substantially parallel to the bottom wall, as shown in FIG. 22. In this region, the inner and outer walls 768 and 770 of the side walls 762 and 764 diverge from one another. Flexible membranes 774 and 776 having a plurality of apertures are disposed between the inner wall 768 and the outer wall 770 at the upper ends of each of the side walls 762 and 764, as shown in FIG. 22. The flexible membranes 774 and 776 are preferably formed of rubber and may be integrally attached to the inner and outer walls 768 and 770 or alternatively may be removable. The flexible membranes 774 and 776 function as sealing strips which prevent leakage of the treatment solution from inside the mouthpiece 760 to the outside environment.

Figure 23:
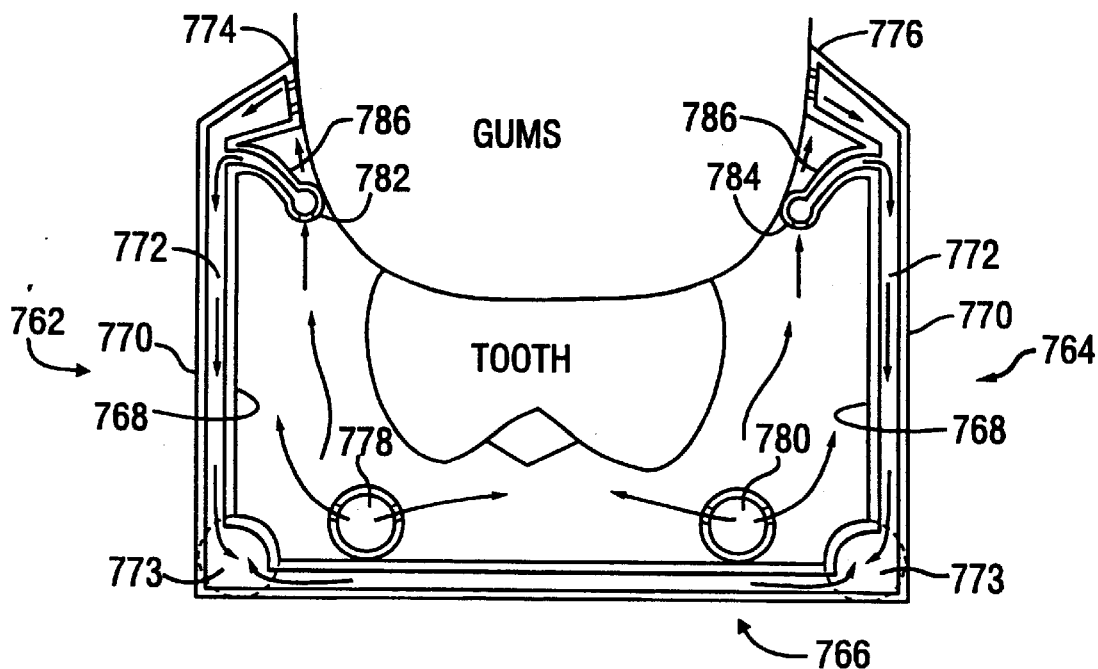
FIG. 23 is a cross-sectional view of the mouthpiece shown in FIG. 21 covering the dentoalveolar structures.

In this embodiment of the present invention, a pair of delivery tubes 778 and 780 are provided along the entire length of the bottom wall 766, as shown in FIG. 21. Each of the pair of delivery tubes 778 and 780 has a plurality of apertures disposed along its entire length through which the treatment solution is discharged toward the teeth and gums, as shown in FIG. 23. A pair of recovery tubes 782 and 784 are also provided along the entire length of the side walls 762 and 764, as shown in FIG. 21. The recovery tubes 782 and 784 may have either a plurality of holes or a cut-out section (not shown) which is disposed along their entire length. The recovery tubes 782 and 784 are designed to abut against the gums (as shown in FIG. 23) and function in much the same way as the recovery ring 38 does in the embodiment shown in FIGS. 14. The recovery tubes 782 and 784'are attached to the inner wall 768 via a conduit 786, as shown in FIG. 22. The conduit 786 provides a fluid communication path between the recovery tubes 782 and 784 and the intake channel 772.

Although the configuration of the mouthpiece 760 is somewhat different from the flexible containment member 100, it functions in much the same way. The treatment solution is delivered to the mouthpiece 760 through the delivery tubes 778 and 780. It exits the apertures in the delivery tubes 778 and 780 striking the covered oral structures at an appropriate velocity and thereby treating them. The spent treatment solution is drawn away from the treatment area through the recovery tubes 782 and 784. Any treatment solution which should by-pass the recovery tubes 782 and 784 will be drawn up into the intake channel 772 through the flexible membranes 774 and 776. Although the recovery tubes 782 and 784 abut the gums, they do not form a hermetic seal with the gums, and therefore some leakage may occur. However, the flexible membranes 774 and 776 do form a hermetic seal with the gums, so that any treatment solution which by-passes the recovery tubes 782 and 784 will be drawn into the intake channel 772 by the suction provided by the suction pump 716.

The construction of the mouthpiece 760 is general and flexible allowing for one size to fit many mouths. This construction provides an increased space over prior art mouthpieces which allows for coverage of all of the dentoalveolar structures, not just the teeth and interdental papillae, as is the case with the prior art devices. This increased space also allows for greater therapeutic benefit via higher fluid volume applied, greater pressure generated, and more turbulence created.

The intake channel 772 is connected to the suction pump 716 via the conduit 742, as shown in FIG. 20. The delivery tubes 778 and 780 are connected to the delivery pump 714 via the conduit 744. The delivery pump 714 and the suction pump 716 are connected to the reservoir 718 via the conduits 748 and 750, respectively.

Figure 24:
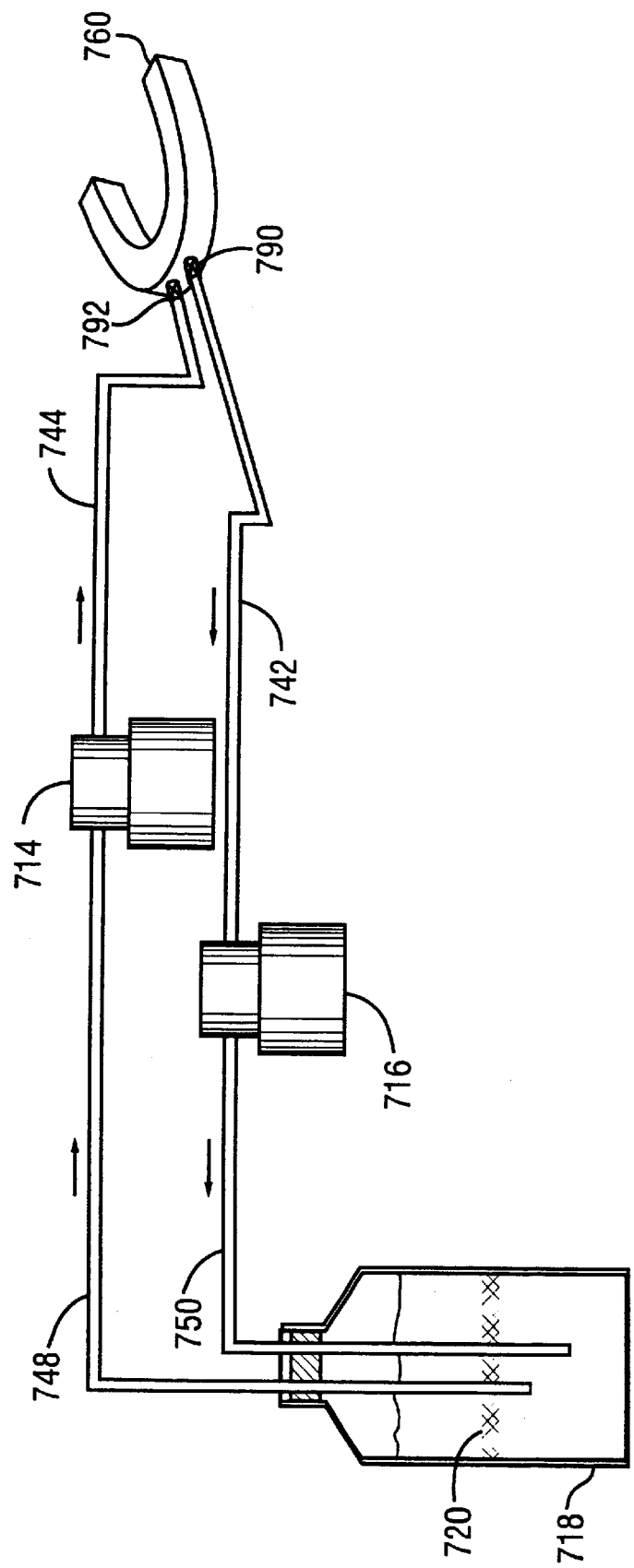
FIG. 24 is a diagram of an alternate embodiment of a recirculating sealed oral irrigation system used for dental treatment according to the present invention.

In an alternate embodiment of the system just described, the mouthpiece 760 is connected to the conduits 742 and 744 at the curved section of the mouthpiece, as shown in FIG. 24. Themoplastic couplings 790 and 792 connect the conduits 742 and 744, respectively, to the mouthpiece 760.

Figure 25:
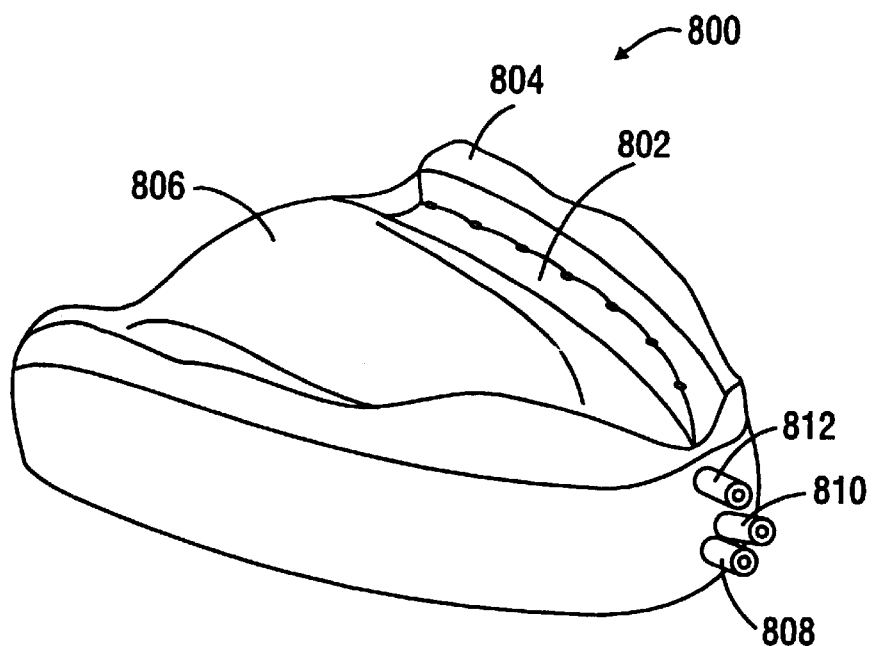
FIG. 25 is a perspective view of another embodiment of a mouthpiece having a three channel design according to the present invention.

Other embodiments of the mouthpiece 760 according to the present invention will now be described. Referring to FIG. 25, an alternate embodiment of the mouthpiece 760 according to the present invention is shown. In this embodiment, the mouthpiece is referred to by reference numeral 800. The mouthpiece 800 is manufactured by preparing a mold of the dentoalveolar structure to be treated and pouring a medical grade silicon material, e.g., Silastic® silicon rubber manufactured by Dow Corning, into the mold. The resultant mouthpiece 800 is generally U-shaped and is defined by a tooth conforming section 802, a gum conforming section 804 and a pallet conforming section 806.

Figure 26:
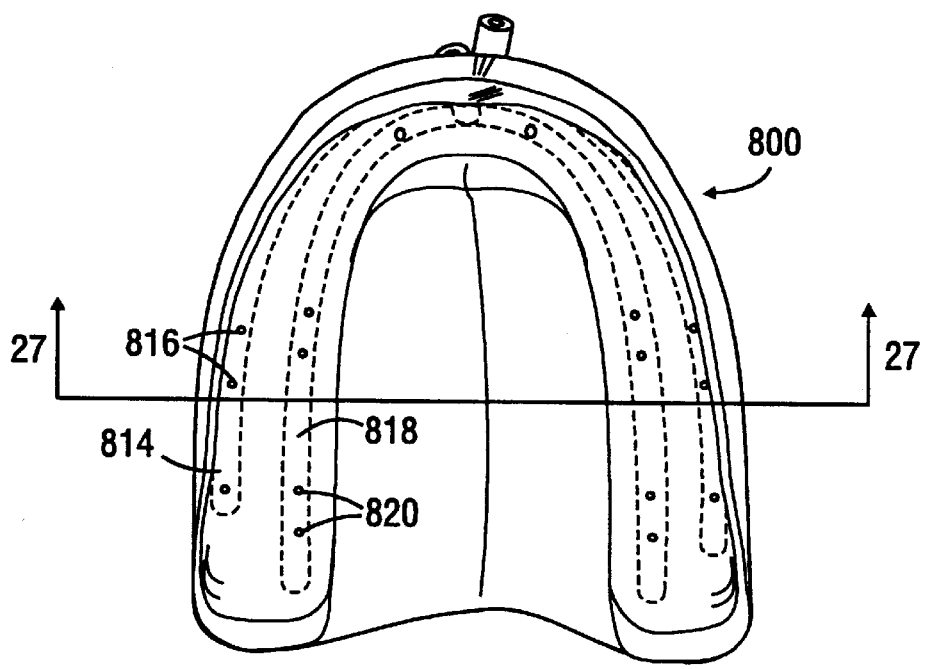
FIG. 26 is a top view of the embodiment of the mouthpiece shown in FIG. 25.

A delivery inlet coupling 808, a recovery outlet coupling 810, and a suction outlet coupling 812 are all coupled to the curved portion of the mouthpiece 800. The delivery inlet coupling 808 delivers treatment solution under pressure to a delivery channel 814 formed along the inner surface of the tooth conforming section 802, as shown in FIG. 26. A plurality of delivery ports 816 are formed along the delivery channel 814 for ejecting the treatment solution into the treatment area. The recovery outlet coupling 810 connects with a recovery channel 818, also formed along the inner surface of the tooth conforming section 802, which removes spent treatment solution from the mouthpiece 800. A plurality of recovery ports 820 are formed along the recovery channel 818 for this purpose.

Figure 27:
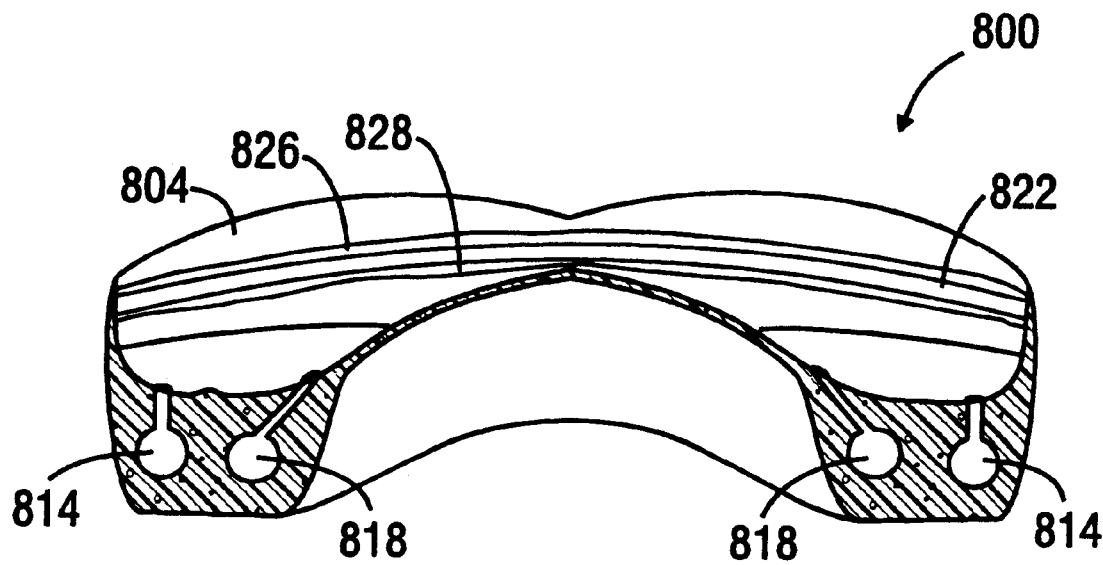
FIG. 27 is a cross-sectional view of the embodiment of the mouthpiece shown in FIG. 26 taken along line 27—27.
Figure 28:
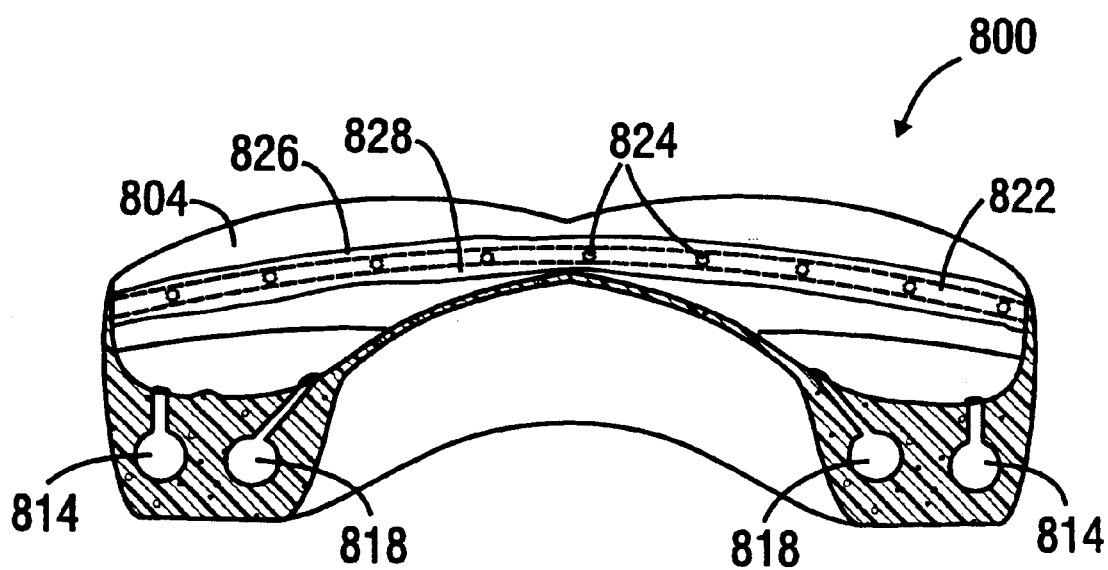
FIG. 28 is a cross-sectional view of an alternate embodiment of the mouthpiece having a three channel design according to the present invention.
Figure 31:
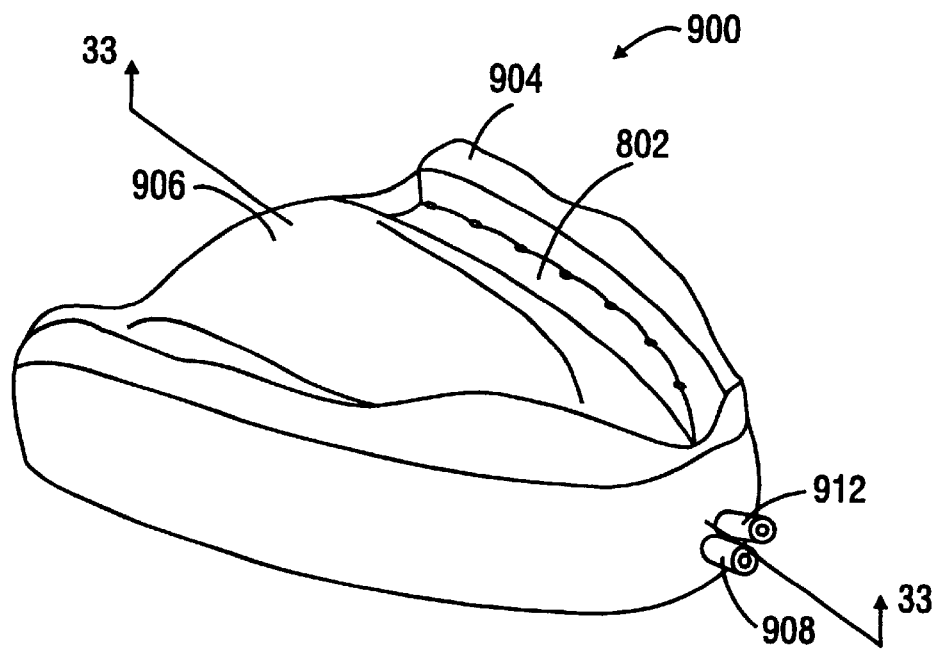
FIG. 31 is a perspective view of another embodiment of a mouthpiece having a two channel design according to the present invention.

The suction outlet coupling 812 connects to a sealing channel 822 that is formed along the entire perimeter of the inner surface of the gum conforming section 804 of the mouthpiece 800. The sealing channel 822 may either be open, as shown in FIG. 27, or it may be closed as shown in FIG. 28. The applications of each embodiment has been previously described. In the embodiment shown in FIG. 28, a plurality of suction ports 824, disposed along the sealing channel 822, supply the suction force to the patients gums for sealing the mouthpiece 800 in place. In the embodiment shown in FIG. 27, the open channel configuration performs this function. The inner surface of the gum conforming section 804 is generally flat and form fits to the gums when a suction force is applied to the sealing channel 822. It is defined by a pair of wing-shaped members 826 and 828 that are disposed on opposite sides of the sealing channel 822, as shown in FIGS. 27 and 28.

In another alternate embodiment of the present invention, the mouthpiece 800 has no recovery channel or corresponding recovery ports, as shown in FIG. 29. Rather, the recovery outlet coupling 810 has a port 830 which opens into the inside of the mouthpiece 800 and allows spent treatment solution to be removed from the treatment area. The embodiment shown in FIG. 29 has an open sealing channel 822. This single recovery port design may also be utilized in the closed sealing channel configuration. This modified embodiment is shown in FIG. 30.

The embodiments shown in FIGS. 25–30 incorporate a three channel design, i.e., the delivery channel 814, recovery channel 818, and sealing channel 822 are separated inside the mouthpiece 800. These embodiments may alternatively incorporate a two channel design. In the two channel design, the recovery channel 818 and the sealing channel 822 are connected to one another inside the mouthpiece 800. This modified design, as it applies to the various embodiments shown in FIGS. 25–30, is shown in FIGS. 31–36.

In the two channel design, there are only two inlets, a suction outlet coupling 912 and a delivery inlet coupling 908. The recovery outlet coupling 810 of the three channel design illustrated in FIGS. 25–30 is incorporated into the suction outlet coupling 912. The suction outlet coupling 912 branches off into two channels, recovery channel 918 and sealing channel 922 at juncture 935, as shown in FIG. 33.

Figure 32:
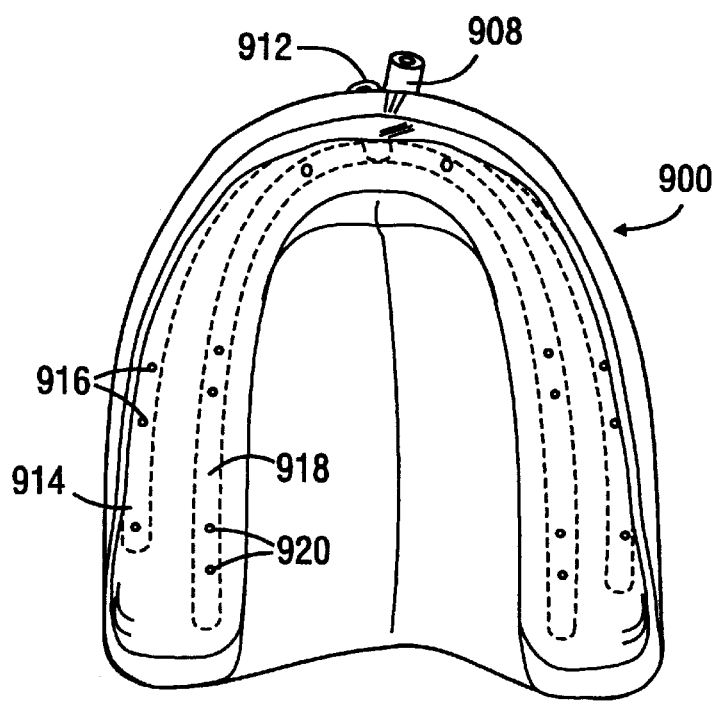
FIG. 32 is a top view of the embodiment of the mouthpiece shown in FIG. 31.
Figure 35:
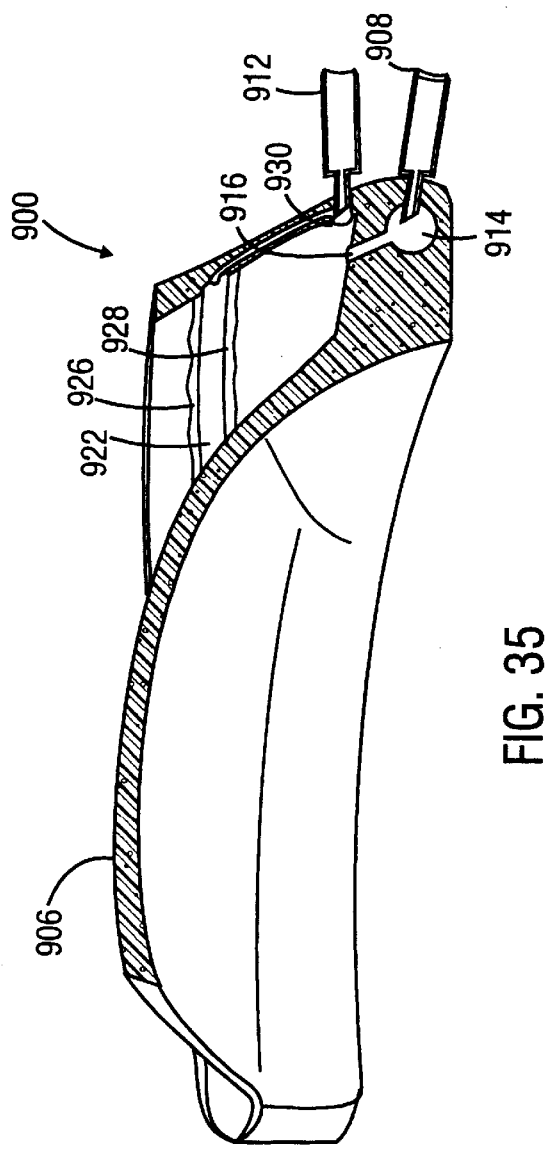
FIG. 35 is a partial cross-sectional partial perspective view of yet another embodiment of the mouthpiece having a two channel design according to the present invention.
Figure 36:
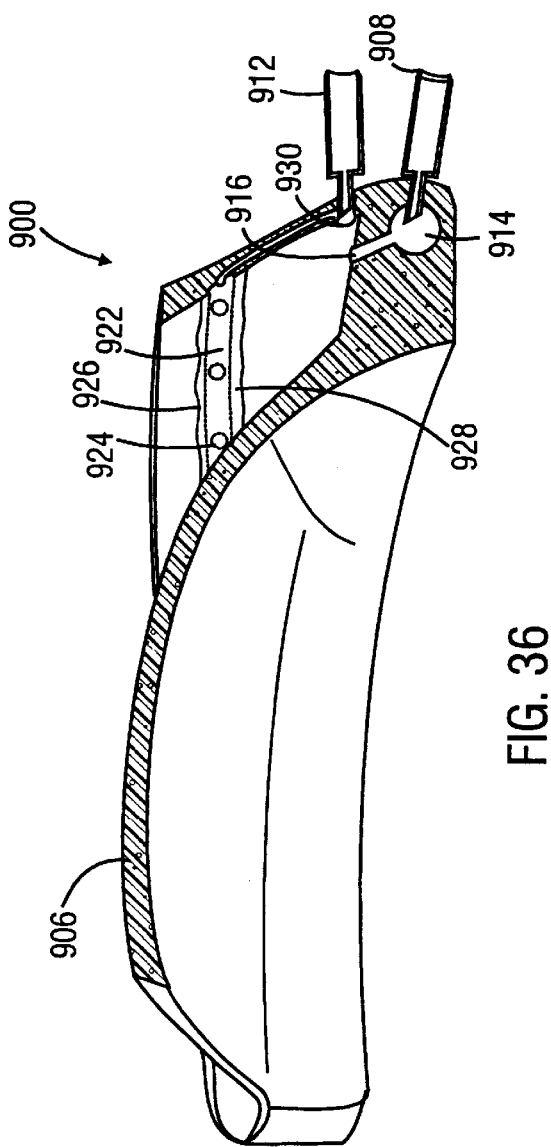
FIG. 36 is a partial cross-sectional partial perspective view of yet another embodiment of the mouthpiece having a two channel design according to the present invention.

In the embodiment shown in FIGS. 32 and 33, the recovery channel 918 has a plurality of ports 920, and the sealing channel 922 is an open channel. In the embodiment shown in FIG. 34, the sealing channel 922 is a closed channel having a plurality of suction ports 924. In the embodiment shown in FIG. 35, the recovery channel 918 and plurality of ports 920 are replaced with a single recovery port 930, and the sealing channel 922 is an open channel. In the embodiment shown in FIG. 36, the recovery channel 918 and plurality of ports 920 are replaced with a single recovery port 930, and the sealing channel 922 is a closed channel having a plurality of suction ports 924.

The mouthpieces 800 and 900 described above, may be connected to the recirculation system as shown in FIG. 20 or the circulation systems shown in FIGS. 16 and 17.

There are a wide variety of uses of the oral application of the present invention. It can be used for aiding in cleaning the teeth of mentally retarded patients with massive dental disease. It can also be used for fluoride treatments for patients of all ages, particularly children and the elderly. Furthermore, it can be used with those having mental or physical disabilities or geriatric patients with arthritis who are not willing or able to perform routine oral hygiene tasks (e.g., brushing and flossing). It can be further used for the delivery of topical medications, such as chlorahexidine, hydrogen peroxide, saline and the like for the prevention and treatment of various oral maladies, particularly periodontal disease. It can be used in conjunction with virtually any type of dental treatment. The possible uses of the system are ever increasing as new medications suitable for oral use are developed.

While the present invention is susceptible to various modifications and alternative forms, a number of which have been discussed above, it should be understood that the invention is not intended to be limited to the particular forms disclosed. For example, although a delivery channel having one or more delivery ports is described in the preferred embodiments, as those of ordinary skill in the art will appreciate, other designs, such as a single delivery port, may be used. It is intended that the present invention cover all modifications, equivalents and alternatives falling within the spirit and scope of the invention as defined by the appended claims.

What is claimed is:

1. A method of irrigating a treatment site with a treatment fluid, comprising the steps of:

(a) sealing the treatment site from an outside environment with a sealing unit utilizing a suction force;

(b) applying the treatment fluid to the treatment site;

(c) removing spent treatment fluid from the treatment site utilizing a recovery unit; and (d) removing any spent treatment fluid which may escape the recovery unit through the sealing unit, so as to prevent leakage of spent treatment solution to the outside environment.

2. The irrigation method as defined in claim 1, further comprising the step of delivering the spent treatment fluid from the treatment site to a reservoir.

3. The irrigation method as defined in claim 2, further comprising the step of purifying the spent treatment fluid.

4. The irrigation method as defined in claim 3, further comprising the step of delivering purified treatment fluid from the reservoir to the treatment site.

5. A method of irrigating a treatment site with a treatment fluid, comprising the steps of:

(a) sealing the treatment site from an outside environment with a sealing unit utilizing a suction force from a first suction source;

(b) applying the treatment fluid to the treatment site;

(c) removing spent treatment fluid from the treatment site utilizing a recovery unit having a second suction source;

(d) removing any spent treatment fluid which may escape the recovery unit through the sealing unit, so as to prevent leakage of spent treatment solution to the outside environment; and (e) repeating steps (a)–(d) sufficiently to rinse the treatment site.

6. The irrigation method defined in claim 5, further comprising the step of delivering the spent treatment fluid from the treatment site to a reservoir.

7. The irrigation method defined in claim 6, further comprising the step of purifying the spent treatment fluid.

8. The irrigation method defined in claim 7, further comprising the step of delivering purified treatment fluid from the reservoir to the treatment site.

9. A method of irrigating a site of a wound or infection with a treatment fluid, comprising the steps of:

(a) sealing the site of wound or infection from an outside environment with a sealing unit utilizing a suction force from a first suction source;

(b) applying the treatment fluid to the site;

(c) removing spent treatment fluid from the site utilizing a recovery unit having a second suction source, the spend treatment fluid including tissue breakdown products and/or infection-generated tissue fluids;

(d) removing any spent treatment fluid which may escape the recovery unit through the sealing unit, so as to prevent leakage of spent treatment solution to the outside environment; and (e) repeating steps (a)–(d) sufficiently to rinse the site and aid in healing the wound or infection.

10. The irrigation method defined in claim 9, further comprising the step of delivering the spent treatment fluid from the treatment site to a reservoir.

11. The irrigation method defined in claim 10, further comprising the step of purifying the spent treatment fluid.

12. The irrigation method defined in claim 11, further comprising the step of delivering purified treatment fluid from the reservoir to the treatment site.

\* \* \* \* \*